United States Patent
Hoffmann et al.

(10) Patent No.: US 9,968,573 B2
(45) Date of Patent: May 15, 2018

(54) ENDOPROSTHESIS HAVING AND ACTIVE SUBSTANCE COATING

(75) Inventors: Erika Hoffmann, Eschweiler (DE); Michael Hoffmann, Eschweiler (DE); Roland Horres, Stolberg (DE); Martin Erdtmann, Julich (DE); Helmut Horbach, Aachen (DE)

(73) Assignee: HEMOTEQ AG, Wurselen (DE)

(*) Notice: Subject to any disclaimer, the term of this patent is extended or adjusted under 35 U.S.C. 154(b) by 1235 days.

(21) Appl. No.: 14/002,223

(22) PCT Filed: Feb. 14, 2012

(86) PCT No.: PCT/DE2012/100035
§ 371 (c)(1),
(2), (4) Date: Aug. 29, 2013

(87) PCT Pub. No.: WO2012/122973
PCT Pub. Date: Sep. 20, 2012

(65) Prior Publication Data
US 2017/0014364 A1    Jan. 19, 2017

(30) Foreign Application Priority Data
Mar. 11, 2011    (DE) .................. 10 2011 014 386

(51) Int. Cl.
| | | |
|---|---|---|
| A61K 31/197 | (2006.01) | |
| A61L 27/54 | (2006.01) | |
| A61L 29/16 | (2006.01) | |
| A61L 31/16 | (2006.01) | |
| A61K 31/7036 | (2006.01) | |
| B05D 1/02 | (2006.01) | |

(52) U.S. Cl.
CPC ........ *A61K 31/197* (2013.01); *A61K 31/7036* (2013.01); *A61L 27/54* (2013.01); *A61L 29/16* (2013.01); *A61L 31/16* (2013.01); *B05D 1/02* (2013.01); *A61L 2300/406* (2013.01); *A61L 2420/02* (2013.01)

(58) Field of Classification Search
CPC .............. A61K 31/197; A61K 31/7036; A61L 2300/406; A61L 2420/02; A61L 27/54; A61L 29/16; A61L 31/16; B05D 1/02
See application file for complete search history.

(56) References Cited

U.S. PATENT DOCUMENTS

| | | | | | |
|---|---|---|---|---|---|
| 2,891,943 | A | * | 6/1959 | Keller .................. | C07C 233/46 536/13.2 |
| 3,230,228 | A | * | 1/1966 | Schnider ................ | A61K 8/42 424/59 |
| 5,120,738 | A | * | 6/1992 | Ikawa ................... | C07C 235/12 514/210.17 |
| 5,756,145 | A | * | 5/1998 | Darouiche .......... | A61F 2/30767 427/2.24 |
| 6,201,009 | B1 | * | 3/2001 | Ozaki .................. | A61K 9/4858 514/452 |
| 6,428,579 | B1 | * | 8/2002 | Valentini ............. | A61F 2/30767 427/2.13 |
| 2002/0150549 | A1 | | 10/2002 | Vogt et al. | |
| 2005/0042240 | A1 | * | 2/2005 | Utterberg ............... | A01N 25/04 424/400 |
| 2008/0058733 | A1 | | 3/2008 | Vogt et al. | |
| 2008/0145392 | A1 | * | 6/2008 | Knaack ................. | A61L 27/227 424/423 |
| 2010/0209472 | A1 | * | 8/2010 | Wang ................... | A61K 31/337 424/423 |
| 2013/0137768 | A1 | * | 5/2013 | Lantoine-Adam .... | C07C 231/12 514/549 |

FOREIGN PATENT DOCUMENTS

| | | |
|---|---|---|
| CN | 101610798 | 12/2009 |
| JP | 2009-538961 | 11/2009 |
| WO | 2007-142629 | 12/2007 |
| WO | 2009051614 | 4/2009 |

OTHER PUBLICATIONS

International Search Report for PCT/DE2012/100035 dated Jun. 14, 2012.
Written Opinion for PCT/DE2012/100035 dated Jun. 14, 2012.

* cited by examiner

*Primary Examiner* — Mark V Stevens
(74) *Attorney, Agent, or Firm* — Amin, Turocy & Watson LLP

(57) ABSTRACT

The present invention relates to an endoprosthesis with a drug coating comprising or consisting of at least one antibiotic agent and at least one further substance having the following general

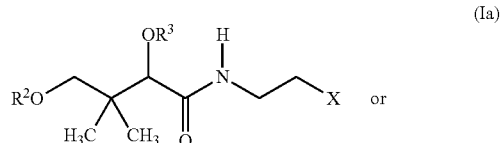

(Ia)

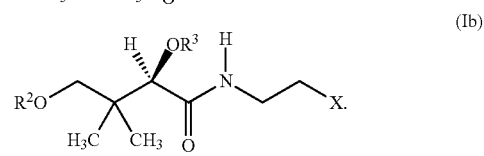

(Ib)

7 Claims, 4 Drawing Sheets

ENDOPROSTHESIS HAVING AND ACTIVE SUBSTANCE COATING

The present invention relates to endoprosthesis having an active agent coating containing or consisting of at least one antibiotic and at least one further substance according to one of the following general formula

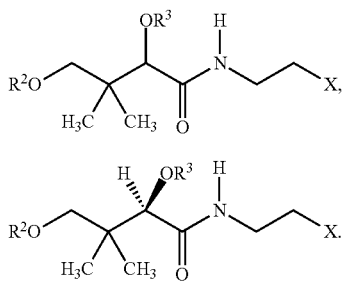

Endoprosthesis are implants that remain permanently or for a longer period in the body and replace the damaged body part in whole or partially. The requirements for such replacement or auxiliary parts are very high and, depending on the conditions at the implantation site, very various. One differs between medical, functional, plastic endoprosthesis, as well as dental implants. Pacemakers, stents and vascular grafts, implants for deep brain stimulation, so-called brain pacemaker, as they are used for example in Parkinson's disease, artificial hearts and port catheter, orthopedic implants like joint replacements or materials that are used for the surgical treatment of bone fractures, visual implant like eye lens, retina, vitreous body, cornea, dental implants, skull reconstruction, bone replacement, penile prostheses, sphincter prostheses, cochlear implants, but also removable function supporting means used for a limited period such as catheters, e.g. urinary catheters, cardiac catheters, breathing hoses, venous catheters, cannulas but also implants only being active agent depots are recognized as implants.

Endoprosthesis are made of biocompatible materials, which can be very different in material and appearance depending on the area of application, and for example consists of metal, metal alloys, plastics or polymers such as PEAK (polyarylether ketones), PEEK (polyether ether ketone), PEK, PEEEK, PEEKEK and PEKK, ceramics but also of combinations thereof. Depending on the material composition and the area of application, the endoprostheses and revision endoprostheses, their percentage of surgical use are not insignificant, are bio-stable, biodegradable, bio-inert or bioactive and have a rough or smooth, microporous or macroporous, hydrophilic or hydrophobic surface, are already coated or pretreated in any other form. The shape of the body to be coated is, in addition to the material itself, important for the coating because the geometric structures may require different coating techniques. Here methods such as dip coating, spray coating, pipetting, electrospinning, etc. as well as combinations of the possible methods can be mentioned, with which the optimal approach for a high quality coating adjusted to the requirements can be achieved and thus influence the success of a therapeutically effective coating positively.

The optimally effective coating of a surface of an endoprosthesis should increase the specified life span of the endoprosthesis or at least increase the necessary residence time in the body and should be able to prevent a revision of the prosthesis, which may be necessary despite optimal prosthetic fit and uncomplicated insertion. The adaptation of the implant to the surrounding tissue should be facilitated through the coating, support a complication-free healing process and promote the acceptance of the foreign body in the organism and preferably prevent or reduce potential disruptive factors that may hinder or prevent the healing process.

For example, orthopedic implants such as for example prosthesis used in the area of bone such as e.g. the hip prosthesis or knee prosthesis should form a strong immediate binding with the host bone. This binding can be improved by coating the surface with a biologically active layer of e.g. hydroxyapatite or other suitable calcium phosphate coatings, which are an essential mineral component of bone. One example of further developments in the field of such bone implant coatings is known under the trade mark Palacos R+G coating of Heraeus which consists of a high-viscose bone cement mixture and gentamicin sulfate. But even here, there are always problems with the acceptance by the host bone and thus this coating is only partially successful, as the elution of the active agent from the matrix does not proceeds dose-adapted and the active agent-free matrix is assumed to be inadequate for further healing process and for long time use conditions of the endoprosthesis. Thus the objective sought is not achieved because, although the revision rates with Palacos R+G are retrogressive, the results are still not satisfying.

In other areas, such as in eye lens implants or on the luminal side of esophageal stents a smooth, hydrophilic, and optimally also acid-resistant surface is required. The optimization of such prostheses by application-oriented coatings is a very broad field, whose development is by no means complete and again and again encounters individual difficulties which have to be conform with the type of disease, the site of the disease, the conditions given and of course the constitution of the patients.

This makes it possible to summarize that although there exists already a large number of variants of coatings for endoprostheses, endoprostheses in all application areas show continuously problems that can not improve the quality of life of patients and cause revision of the implant. The causes of complications are various and can be divided roughly into two groups:
1. Surgical technique, material defects, design problems in general but also due to individually occurring biological diversifications, etc.
2. Generally unfavorable adaption processes of different origin, bone- or cartilage abrasion, inflammation, bacterial colonization, immune system reactions to foreign bodies.

The coating of endoprostheses with pure antibiotics without additives or matrix shows no success, because on the one hand the antibiotic dissolves in the shortest time and on the other hand no layer adhering to the endoprosthesis can be prepared with the substance because the coating powdery, dry, brittle and crumbly. Consequently, it cannot be shown how much of the antibiotic reaches the target site and can be effective. Under these conditions, the therapeutic effect due to a lack of precision and reproducibility of the released minimum amounts and concluding the effectiveness of the coated stent is put into question. These deficits cannot meet approximately the different, claimed requirements at the implantation site and guarantees under no circumstances an adequate, optimal, and trouble free healing process. FIGS. 4a and 4b show the brittle surface of an endoprosthesis spray-coated with gentamicin sulfate. FIGS. 4a and 4b show clearly the non-rigid, brittle, crumbly gentamicin sulfate coating, where the gentamicin sulfate does not adhered permanently to the surface of the medical device and therefore the coating easily flakes off and is altogether unsuitable to provide a medical device with a coating, which fulfils the requirements of a medical product, its storage, sterilization and regulatory approval requirements.

A coating of endoprostheses obtained from gentamicin sulfate, and the higher-chain unsaturated fatty acid palmitic acid (C16:0) unfortunately shows no controlled in vitro release of gentamicin palmitate and high concentrations eluted at the beginning without apparent release delay. In addition, only up to 58% of the gentamicin sulfate are released, which with an insufficient therapeutic effect is achieved, too. The gentamicin sulfate thus forms a fragile and brittle coating that flakes off already during sterilization and packaging of the coated medical device, and on the other hand areas of the coating adhere so strongly on the surface of the implant, that from these areas nearly no gentamicin is released, so that finally only slightly higher than 50% release of gentamicin is obtained. Therefore, the gentamicin sulfate coating is not suitable for application and release of the antibiotic gentamicin from a surface of a medical device. Moreover, in addition to the inadequate release of the antibiotic, despite or even because of the better adhesion, especially of the antibiotic in a palmitate matrix on the endoprosthesis the toxicity of palmitic acid has to be classified as very precarious, as palmitic acid is also found to be cytotoxic and therefore is not suitable as an optimal matrix for the antibiotic and as such hinders the further course of healing, which is noticeable especially in the field of bone implants, since the removal or diffusion and diffusion rate of substances into the environment varies in particular compared to an implant in fluid carrying environment. Objective of the present invention is it to provide coated endoprostheses, which avoid or decrease significantly the known disadvantages after implantation or fulfil the minimum necessary requirements to be met by an endoprosthesis to guarantee an uncomplicated process of healing and unproblematic long-lasting use. This objective is solved by the technical teaching of the independent claims of the present invention. Further advantageous embodiments of the invention are evident from the dependent claims, the description and the examples.

It has been found that the aforementioned disadvantages which result after implantation of endoprostheses and particularly of bone-contacting implants can be avoided or reduced by an active agent coating containing or consisting of at least one antibiotic and at least one substance of the general formula (Ia) and/or (Ib)

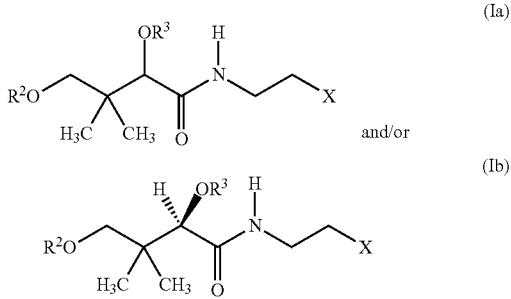

wherein
X means —COOH, —COOR$^1$, —CH$_2$OH, —CH$_2$OR$^1$,
R$^2$ and R$^3$ mean independently of each other —COOR$^4$, —COOR$^5$, —COR$^4$, —COR$^5$, —R$^4$, —R$^5$, —H;

R$^1$, R$^4$ and R$^5$ represent independently of each other —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —CH(CH$_3$)—C(CH$_3$)$_3$, —C$_7$H$_{15}$, —C$_3$H$_6$—C(CH$_3$)$_3$, —C$_4$H$_8$—CH(CH$_3$)$_2$, —C$_8$H$_{17}$, —C$_4$H$_8$—C(CH$_3$)$_3$, —C$_5$H$_{10}$—CH(CH$_3$)$_2$, —C$_9$H$_{19}$, —C$_5$H$_{10}$—C(CH$_3$)$_3$, —C$_6$H$_{12}$—CH(CH$_3$)$_2$, —C$_{10}$H$_{21}$, —C$_6$H$_{12}$—C(CH$_3$)$_3$ and —C$_7$H$_{14}$—CH(CH$_3$)$_2$, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH=CH$_2$, —C$_3$H$_6$—CH=CH$_2$, —C$_2$H$_4$—CH=CH—CH$_3$, —CH$_2$—CH=CH—C$_2$H$_5$, —CH=CH—C$_3$H$_7$, —CH$_2$—CH=CH—CH=CH$_2$, —CH=CH—CH=CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —C$_2$H$_4$—C(CH$_3$)=CH$_2$, —CH$_2$—CH(CH$_3$)—CH=CH$_2$, —CH(CH$_3$)—CH$_2$—CH=CH$_2$, —CH$_2$—CH=C(CH$_3$)$_2$, —CH$_2$—C(CH$_3$)=CH—CH$_3$, —CH(CH$_3$)—CH=CH—CH$_3$, —CH=CH—CH(CH$_3$)$_2$, —CH=C(CH$_3$)—C$_2$H$_5$, —C(CH$_3$)=CH—C$_2$H$_5$, —C(CH$_3$)=C(CH$_3$)$_2$, —C(CH$_3$)$_2$—CH=CH$_2$, —CH(CH$_3$)—C(CH$_3$)=CH$_2$, —C(CH$_3$)=CH—CH=CH$_2$, —CH=C(CH$_3$)—CH=CH$_2$, —CH=CH—C(CH$_3$)=CH$_2$, —C$_4$H$_8$—CH=CH$_2$, —C$_3$H$_6$—CH=CH—CH$_3$, —C$_2$H$_4$—CH=CH—C$_2$H$_5$, —CH$_2$—CH=CH—C$_3$H$_7$, —CH=CH—C$_4$H$_9$, —C$_3$H$_6$—C(CH$_3$)=CH$_2$, —C$_2$H$_4$—CH(CH$_3$)—CH=CH$_2$, —CH$_2$—CH(CH$_3$)—CH$_2$—CH=CH$_2$, —CH(CH$_3$)—C$_2$H$_4$—CH=CH$_2$, —C$_2$H$_4$—CH=C(CH$_3$)$_2$, —C$_2$H$_4$—C(CH$_3$)=CH—CH$_3$, —CH$_2$—CH(CH$_3$)—CH=CH—CH$_3$, —CH(CH$_3$)—CH$_2$—CH=CH—CH$_3$, —CH$_2$—CH=CH—CH(CH$_3$)$_2$, —CH$_2$—CH=C(CH$_3$)—C$_2$H$_5$, —CH$_2$—C(CH$_3$)=CH—C$_2$H$_5$, —CH(CH$_3$)—CH=CH—C$_2$H$_5$, —CH=CH—CH(CH$_3$)—C$_2$H$_5$, —CH=CH—CH$_2$—CH(CH$_3$)$_2$, —CH=C(CH$_3$)—C$_3$H$_7$, —C(CH$_3$)=CH—C$_3$H$_7$, —CH$_2$—CH(CH$_3$)—C(CH$_3$)=CH$_2$, —CH(CH$_3$)—CH$_2$—C(CH$_3$)=CH$_2$, —CH(CH$_3$)—CH(CH$_3$)—CH=CH$_2$, —CH$_2$—C(CH$_3$)$_2$—CH=CH$_2$, —C(CH$_3$)$_2$—CH$_2$—CH=CH$_2$, —CH$_2$—C(CH$_3$)=C(CH$_3$)$_2$, —CH(CH$_3$)—CH=C(CH$_3$)$_2$, —C(CH$_3$)$_2$—CH=CH—CH$_3$, —CH(CH$_3$)—C(CH$_3$)=CH—CH$_3$, —CH=C(CH$_3$)—CH(CH$_3$)$_2$, —C(CH$_3$)=CH—CH(CH$_3$)$_2$, —C(CH$_3$)=C(CH$_3$)—C$_2$H$_5$, —CH=CH—C(CH$_3$)$_3$, —C(CH$_3$)$_2$—C(CH$_3$)=CH$_2$, —CH(C$_2$H$_5$)—C(CH$_3$)=CH$_2$, —C(CH$_3$) (C$_2$H$_5$)—CH=CH$_2$, —CH(CH$_3$)—C(C$_2$H$_5$)=CH$_2$, —CH$_2$—C(C$_3$H$_7$)=CH$_2$, —CH$_2$—C(C$_2$H$_5$)=CH—CH$_3$, —CH(C$_2$H$_5$)—CH=CH—CH$_3$, —C(C$_4$H$_9$)=CH$_2$, —C(C$_3$H$_7$)=CH—CH$_3$, —C(C$_2$H$_5$)=CH—C$_2$H$_5$, —C(C$_2$H$_5$)=C(CH$_3$)$_2$, —C[(C(CH$_3$)$_3$]=CH$_2$, —C[CH(CH$_3$)(C$_2$H$_5$)]=CH$_2$, —C[CH$_2$—CH(CH$_3$)$_2$]=CH$_2$, —C$_2$H$_4$—CH=CH—CH=CH$_2$, —CH$_2$—CH=CH—CH$_2$—CH=CH$_2$, —CH=CH—C$_2$H$_4$—CH=CH$_2$, —CH$_2$—CH=CH—CH=CH—CH$_3$, —CH=CH—CH$_2$—CH=CH—CH$_3$, —CH$_2$—CH=CH—C(CH$_3$)=CH$_2$, —CH$_2$—CH=C(CH$_3$)—CH=CH$_2$, —CH$_2$—C(CH$_3$)=CH—CH=CH$_2$, —CH(CH$_3$)—CH=CH—CH=CH$_2$, —CH=CH—CH$_2$—

C(CH₃)=CH₂, —CH=CH—CH(CH₃)—CH=CH₂, —CH=C(CH₃)—CH₂—CH=CH₂, —C(CH₃)=CH—CH₂—CH=CH₂, —CH=CH—CH=C(CH₃)₂, —CH=CH—C(CH₃)=CH—CH₃, —CH=C(CH₃)—CH=CH—CH₃, —C(CH₃)=CH—CH=CH—CH₃, —CH=C(CH₃)—C(CH₃)=CH₂, —C(CH₃)=CH—C(CH₃)=CH₂, —C(CH₃)=C(CH₃)—CH=CH₂, —CH=CH—CH=CH—CH=CH₂, —C₅H₁₀—CH=CH₂, —C₄H₈—CH=CH—CH₃, —C₃H₆—CH=C(CH₃)₂, —C₆H₁₂—CH=CH₂, —C₅H₁₀—CH=CH—CH₃, —C₄H₈—CH=C(CH₃)₂, —C₇H₁₂—CH=CH₂, —C₆H₁₂—CH=CH—CH₃, —C₅H₁₀—CH=C(CH₃)₂, —C₈H₁₄—CH=CH₂, —C₇H₁₄—CH=CH—CH₃ and —C₆H₁₂—CH=C(CH₃)₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —CH₂—CH(CH₃)—C≡CH, —CH(CH₃)—CH₂—C≡CH, —CH(CH₃)—C≡C—CH₃, —C₄H₆—C≡CH, —C₃H₆—C≡C—CH₃, —C₂H₄—C≡C—C₂H₅, —CH₂—C≡C—C₃H₇, —C≡C—C₄H₉, —C₂H₄—CH(CH₃)—C≡CH, —CH₂—CH(CH₃)—CH₂—C≡CH, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —C≡C—C(CH₃)₃, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —CH₂—C≡C—C≡C—CH₃, —C≡C—CH₂—C≡C—CH₃, —C≡C—C≡C—C₂H₅, —C≡C—CH(CH₃)—C≡CH, —CH(CH₃)—C≡C—C≡CH, —CH(C≡CH)—CH₂—C≡CH, —C(C≡CH)₂—CH₃, —CH₂—CH(C≡CH)₂, —CH(C≡CH)—C≡C—CH₃, —C₅H₁₀—C≡CH, —C≡C—C₆H₁₃, —C₅H₁₀—C≡C—CH₃, —C₆H₁₂—C≡CH, —C≡C—C₇H₁₅, —C₆H₁₂—C≡C—CH₃, —C₇H₁₄—C≡CH, —C≡C—C₈H₁₇, —C₇H₁₄—C≡C—CH₃ and —C₈H₁₆—C≡CH,

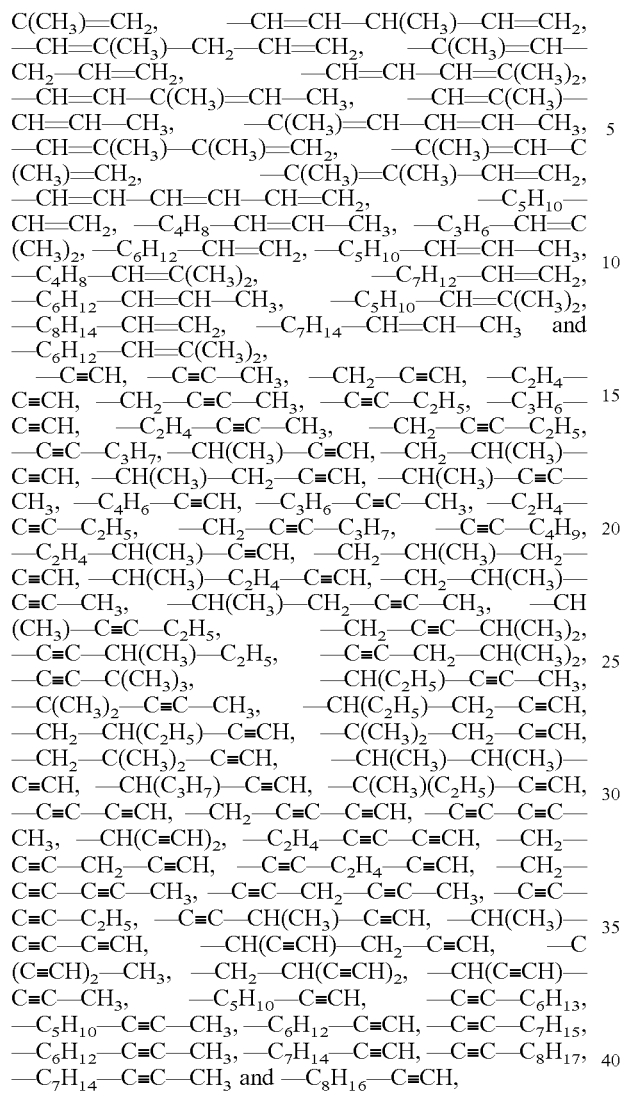

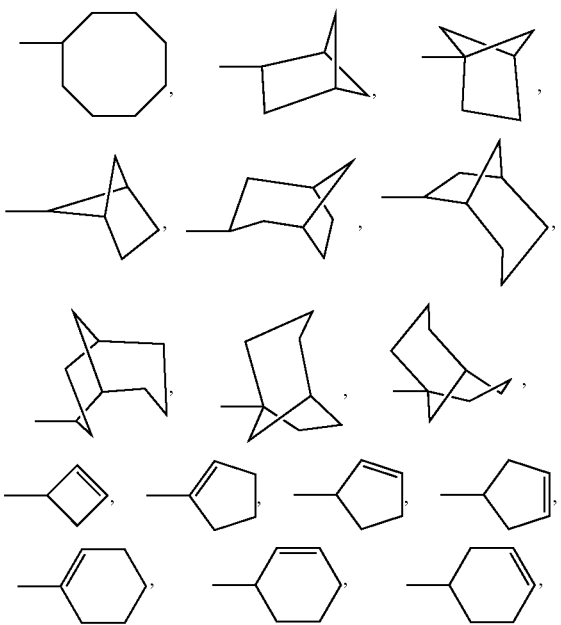

as well as salts, hydrates, solvates, enantiomers, diastereomers, racemates, mixtures of enantiomers and mixtures of diastereomers of the above mentioned compounds.

Surprisingly it has been found that the coating according to the invention consisting of at least one antibiotic and at least one substance of the general formula (Ia) and/or (Ib) are characterized by a preferred elution kinetic. The antibiotic is released quickly and completely from the coating. In addition the coating is characterized by a reduced brittleness and fragility and a better adhesion to the endoprosthesis despite complete release so that the risk of detachment of the coating during transportation, storage, sterilization or implantation is reduced remarkably.

Preferred Compounds

It has been found that coatings comprising or consisting of at least one antibiotic and at least one substance according to one of the following general formulas are especially preferred:

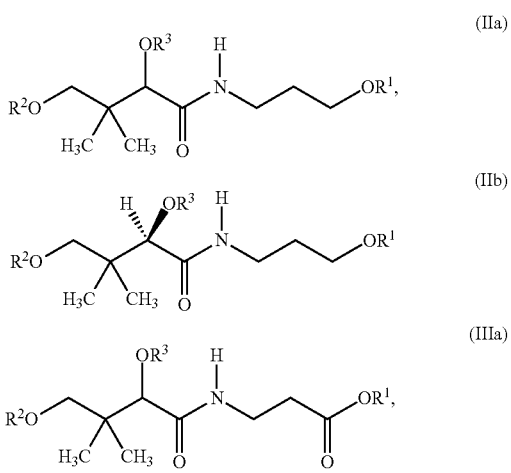

-continued

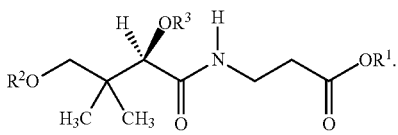
(IIIb)

wherein R¹, R² and R³ have the meaning as defined above.

Even more preferred is a coating comprising or consisting of an antibiotic and dexpanthenol or pantothenic acid as well as pantoic acid or pontocaine and/or its derivatives like formiate, acetate, propionate, ethylester or ethylether. Especially preferred is also a coating comprising or preferably consisting of at least one amino glycoside antibiotic with pantothenic acid or dexpanthenol or the above mentioned derivatives thereof.

Pantothenic acid ((R)—N-(2,4-dihydroxy-3,3-dimethyl-1-oxobutyl)-(3-alanin) is a vitamine from the group of the B-vitamines (vitamine B5), which is resorbed from nutrients and as part of the acyltransferase Coenzyme A has an essential role in metabolism. One can find pantothenic acid preferentially as ingredient of hair care products and products against acne. Pantothenic acid can be illustrated by one of the following formulas:

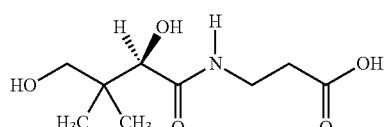
(IVa)

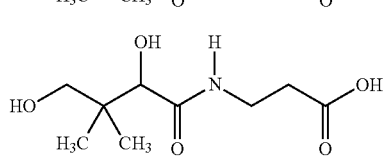
(IVb)

Dexpanthenol (also called Pantothenol, Panthenol, D-Panthenol) with the systemical name (+)-(R)-2,4-dihydroxy-N-(3-hydroxypropyl)-3,3-dimethyl-butanamide and the following structural formula

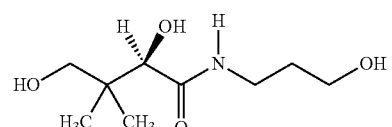
(Va)

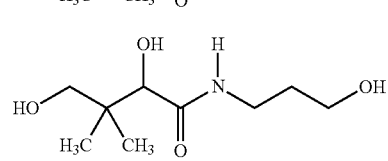
(Vb)

is used for a long time as agent against skin- and mucous membrane diseases and in cosmetics as it has anti-pruritic, anti-inflammatory, wound healing enhancing and cell formation stimulating characteristics and is resorbed well by the skin as additive in water-oil emulsions, wherein it accumulates at the application site and due to its hydrophilic properties increases the moisture retention ability of the skin and improves the elasticity of the skin and thus besides to the nourishing properties supports the regeneration of skin cells, thus contributing to the regeneration. Therefore wound healing preparations to be topically applied such as burn and wound gels, wound ointments, eye and nasal ointments, nasal sprays, vein ointments, moth gels, ointments for the treatment of hemorrhoids, acne preparations, care creams for dry inflamed skin belong to the dexpanthenol-containing products. It is therefore also found in lozenges for sore throat and injection solutions.

Within the body it is used as a component of vitamin preparations in the form of capsules, tablets and injectable solutions and in contact lens cleaning products. Dexpanthenol is converted in the body to pantothenic acid (vitamin B5) also preferred as a coating component and is therefore also applicable for coating prostheses.

Antibiotics which can be used in the coating according to the invention comprises among others penicillin, penicillin G and V, amikacin, amoxicillin, ampicillin, bacampicillin, carbenicillin, indanyl pivmecillinam, oxacillin, flucloxacillin, aminopenicilline, aminocumarine, azithromycin, mezlocillin, piperacillin, azlocillin, temocillin, ticarcillin, amoxicillin, clavulansaure, ampicillin, sulbactam, piperacillin, tazobactam, sulbactam, cephalosporins, cefazolin, cefamandol, cefotiam, cefuroxime, cefmenoxime, cefodizime, cefoperazone, cefotaxime, ceftazidime, cefsulodin, ceftriaxone, cefepime, cefpirome, cefoxitin, cefotetan, cefaclor, cefadroxil, cefalexin, cefuroxim axetil, cefixime, cefpodoxime, ceftibuten, chlorhexidine, imipenem, gramidicin, kanimycin, cethromycin, narbomycin, telithromycin, lincomycin, meropenem, ertapenem, doripenem, aztreonam, josamycin, erythromycin, roxithromycin, clarithromycin, spiramycin, polymyxin B, azithromycin, telithromycin, quinopristin, dalfopristin, clindamycin, tetracycline, oxytetracycline, doxycycline, minocycline, trimethoprim, tyrothricin, sulfamethoxazole, sulfametrole, nitrofurantoin, lomefloxacin, norfloxacin, ciprofloxacin, ofloxacin, fleroxacin, levofloxacin, ofloxacin, enoxacin, fosmidomycin, sparfloxacin, methicillin, tinidazole, moxifloxacin, vancomycin, teicoplanin, linezolid, daptomycin, rifampicin, fusidic acid, fosfomycin, trometamole, chloramphenicol, metronidazole, colistin, mupirocin, bacitracin, neomycin, netilmycin, tigecycline, sulfasalazine, sulfadiazine, sulfadoxine, fluconazole, itraconazole, voriconazole, posaconazole, pyrimethamine, trimethoprim, amphotericin B, 5-flucytosine, caspofungin and/or anidulafungin.

Especially preferred are inhibitors of the cell wall synthesis such as imipenem, meropenem, ertapenem, aztreonam, pencilline, aminpenicillins, acylaminopenicillins, isoxazolylpenicillins, cephalosporins, sultamicillin, fosfomycin, glycopeptide such as vancomycin and teicoplanin, polypetides such as bacitracin, colistin, gramicidin, polymyxin B, tyrothricin and of the protein synthesis at the ribosome such as antibiotics from the group of amino glycosides also called amino glycoside-antibiotics. The group of amino glycosides which is especially preferred for a coating according to the invention comprises or consist of: streptomycin, neomycin, framycetin, paromomycin, ribostamycin, kanamycin, amikacin, arbekacin, bekanamycin, dibekacin, tobramycin, spectinomycin, hygromycin B, paromomycinsulfat, gentamicin, netilmicin, sisomicin, isepamicin, verdamicin, astromicin, apramycin, ansamycine such as for example rifampicin, geneticin. An especially preferred amio glycoside is gentamicin (mixture of types) as well as all single compounds which belong to the group of getamicins, like gentamicin B (betamicin) or gentamicin C₁. The active agent used pharmaceutically consists of several individual compounds of the group of substances of gentamicins, contained are almost exclusively gentamicins of type C. Unless otherwise indicated in the following the term gentamicin means always this mixture of types.

Amino glycosides belong to the group of oligosaccharide antibiotics, with combinations of amino sugar- and cyclohexane building blocks. Excretion occurs mainly by the kidneys with a short half-life of about two hours.

Further preferred antibiotics are: daptomycin, tigecycline, chloramphenicol, doxycycline, monocycline, tetracycline, oxytetracycline, azithromycin, clarithromycin, erythromycin, roxithromycin, dalfopristin, quinupristin, clindamycin, lincomycin, telithromycin, narbomycin, cethomycin and fusidinic acid.

It is also possible that combinations of at least two antibiotics are comprised by a coating of the present invention These could be present together in one layer of the coating or arranged in separate layers one above the other, or may be applied in different areas of the prosthesis.

The choice of antibiotic and its concentration depends on the infection normally occurring in connection with the coated endoprosthesis most often and possibly also the known incompatibilities of the patient to be treated.

The antibiotics used may be of organic, semi-synthetic and synthetic origin.

With the help of an active agent coating according to the invention, complaints that may occur after implantation, e.g. the rate of revision, hence, the early removal of an endoprosthesis such as a hip joint prosthesis, can be reduced considerably. Primarily infections caused by gram-positive organisms and gram-negative enteric bacteria, and non-enteric bacteria are thus ideally prevented but at least minimized to an acceptable form such that the body can tackle successfully the few eventually remaining microbes.

It is preferred that the entire endoprosthesis is coated uniformly. Furthermore, it is preferred when a uniform distribution of the antibiotic and at least one substance of the formula (Ia) and/or (Ib) is present on the endoprosthesis.

In general an entire active agent coating of the endoprosthesis is advantageous, i.e. the entire surface of the endoprosthesis is provided with a coating. The coating of the endoprosthesis can further still be arranged to the effect that the coating with the mixture of the antibiotic and the substance of the formula (Ia) and/or (Ib) is not uniformly formed, but using a gradient that means a concentration gradient on the endoprosthesis is generated. Thus a greater concentration of the antibiotic and the substance of the formula (Ia) and/or (Ib) can be applied for example in the middle or at certain areas of the endoprosthesis, as on the remaining areas of the endoprosthesis.

Additionally a higher concentration of the antibiotics and of the substance of the formula (Ia) and/or (Ib) than on the remaining surface can also be applied to only one side or to one part of the endoprosthesis. Any variations are possible here.

The term "coating" or "active agent coating" is intended to include not only a surface coating but also filling or coating of folds, cavities, pores, micro-needles or other fillable areas on or between or in the endoprosthesis.

The surface may be additionally provided with a hemocompatible layer as a base coat that is applied by covalent immobilization of semi-synthetic heparin derivatives such as desulfated, reacetylated heparin, or chitosan derivatives, such as N-carboxymethylated, partially N-acetylated chitosan.

All endoprostheses can be provided with such a coating. It is also possible to partially coat the endoprostheses.

To the coating of the at least one antibiotic and the substance of the general formula (Ia) or (Ib), one or more further active agents, preferably an anti-inflammatory, antineoplastic, anti-angiogenic, anti-proliferative or immunosuppressive substance may be admixed.

Usable anti-phlogistic, anti-neoplastic, anti-angiogenic, anti-proliferative or immunosupressive substances are among others sirolimus (rapamycin), everolimus, pimecrolimus, somatostatin, tacrolimus, roxithromycin, dunaimycin, ascomycin, bafilomycin, erythromycin, midecamycine, josamycin, concanamycin, clarithromycin, troleandomycin, folimycin, cerivastatin, simvastatin, lovastatin, fluvastatin, rosuvastatin, atorvastatin, pravastatin, pitavastatin, vinblastine, vincristine, vindesine, vinorelbine, etobosid, teniposide, nimustine, carmustine, lomustine, cyclophosphamide, 4-hydroxyoxy cyclophosphamide estramustine, melphalane, betulinic acid, camptothecin, lapachole, β-lapachone, podophyllotoxin, betulin, tropfosfamid, podophyllic acid-2-ethylhydrazide, ifosfamid, chlorambucil, bendamustine, dacarbazine, busulfan, procarbazine, treosulfan, tremozolomid, thiotepae, daunorubicin, doxorubicin, aclarubicin, epirubicin, mitoxantrone, idarubicin, bleomycin, mitomycin, dactinomycin, methotrexate, fludarabine, fludarabine-5'-dihydrogenphosphaet, mofebutazone, acemetacin, diclofenac, lonazolac dapsone, o-carbamoylphenoxyacetic acid, lidocaine, ketoprofen, mefenamic acid, piroxicam, meloxicam, chloroquine, penicillamine, hydroxychloroquine, auranofin, sodium aurothiomalate, oxaceprol, celecoxib, β-sitosterol, ademetionin, myrtecain, polidocanol, nonivamide, levomenthol, benzocaine, aescin, cladribine, mercaptopurine, thioguanine, cytarabine, fluorouracil, gemcitabine, capecitabine, docetaxel, carboplatin, cisplatin, oxaliplatin, amsacrine, irinotecan, topotecan, hydroxyurea, miltefosine, pentostatin, aldesleukin, tretinoin, asparaginase, pegasparase, anastrozole, exemestane, letrozole, formestane, Aminoglutethemid, adriamycin, azithromycin, spiramycin, cepharantin, SMC proliferation inhibitor-2w, epothilones A and B, mitoxanthrone, azathioprine, mycophenolate mofetil, c-myc antisense, b-myc antisense selectin (cytokine antagonist), CETP inhibitor, cadherins, cytokine inhibitors, COX-2 inhibitor, NFkB, angiopeptin, ciprofloxacin, camptothecin, fluroblastin, monoclonal antibodies, which inhibit the muscle cell proliferation, bFGF antagonists, probucol, prostaglandins, folic acid and derivatives, vitamins of the B series, vitamin D derivatives such as calcipotriol and tacalcitol, thymosin D-1, fumaric acid and its derivatives such as dimethyl fumarate, IL-1 beta inhibitor, colchicine, NO donors such as pentaerythrityltetranitrat and syndnoeimine, S-nitrosated derivatives, tamoxifen, staurosporine, beta-estradiol, α-estradiol, estrone, estriol, ethinylestradiol, fosfestrol, medroxyprogesterone, estradiolcypionate, estradiolbenzoate, tranilast, kamebakaurin and other terpenoids, which are used in cancer therapy, verapamil, tyrosine kinase inhibitors (tyrphostins), cyclosporine A, paclitaxel and derivatives thereof, (6-a-hydroxy-paclitaxel, baccatin, taxotere, etc.), macrocyclic oligomers of carbon suboxide (MCS) obtained synthetically produced as well as from native sources and derivatives thereof, molgramostim (rhuGM-CSF), peginterferon a-2b, lanograstim (r HuG-CSF) filgrastim, macrogol, dacarbazine, basiliximab, daclizumab, ellipticine, D-24851 (Calbiochem), colcemid, cytochalasin AE, Indanocine, nocadazole, S 100 protein, PI-88, melanocyte stimulating hormone (α-MSH), bacitracin, vitronectin receptor antagonists, azelastine, guanidylcyclase stimulator, tissue inhibitor of metalloproteinase-1 and 2, free nucleic acids, nucleic acids incorporated into virus transmitters, DNA and RNA fragments, plasminogen activator inhibitor-1, plasminogen activator inhibitor-2, antisense oligonucleotides, VEGF inhibitors, IGF-1 mentioned. Positive influence on the postoperative phase have also anticoagulants such as argatroban, aspirin, abciximab, synthetic antithrombin, bivalirudin, coumadin, enoxoparin, Hemoparin® (desulfated and N-reacetylated heparin), tissue plasminogen activator, GPIIb/IIIa platelet membrane receptor, factor Xa-inhibitor, activated protein C, antibodies, heparin, hirudin, r-hirudin, PPACK, protamine, prourokinase, streptokinase, warfarin, urokinase, vasodilators such as dipyridamole, trapidil, nitroprusside, PDGF antagonists such as triazolopyrimidine and Seramin, ACE inhibitors such as captopril, cilazapril, lisinopril, enalapril, losartan, thioprotease inhibitors, caspase inhibitors, apoptosis inhibitors, apoptosis regulators such as p65, NF-kB and Bcl-xL antisense oligonucleotides and prostacyclin vapiprost, a-, β- and γ-interferon, histamine antagonists, serotonin blockers, halofuginone, nifedipine, tocopherol, tranirast, molsidomine, tea polyphenols, epicatechin gallate, epigallocatechin gallate, boswellic acids and their derivatives, leflunomide, anakinra, etanercept, sulfasalazine, etoposide, dicloxacyllin, tetracycline, triamcinolone, mutamycin, procainimid, retinoic acid, quinidine, disopyrimid, flecainide, propafenone, sotolol, amidoron. Other drugs are steroids (hydrocortisone, betamethasone, dexamethasone), nonsteroidal agents (NSAIDS) such as fenoprofen, ibuprofen, indomethacin, naproxen, phenylbutazone and others. Antiviral agents such as acyclovir, ganciclovir and zidovudine are also used. Various antifungal agents are used in this field. Examples include clotrimazole, flucytosine, griseofulvin, ketoconazole, miconazole, nystatin, terbinafine. Furthermore, an additional active agent layer comprising a anti-inflammatory, antineoplastic, anti-angiogenic, anti-proliferative and immunosuppressive substance are above or below the layer of the compound of the invention. The additional active agent layer may consist of pure drug, or additional drug can be incorporated into a polymeric coating. Corresponding polymers are further enumerated below. The choice of the active agent and the concentration thereof depends on the individual symptoms and the resulting therefrom needs to be able to promote the healing of a patient.

If necessary, the inventive coating may be applied to an existing lower layer (base layer). It is preferably a base coat of biostable or biodegradable polymers or of calcium phosphate (for example hydroxyapatite) or of ceramic materials. Such materials may also be admixed to the coating of the present invention or may be applied as a top layer above a coating of the invention, wherein also in said base coat or top layer an antibiotic may be present, preferably dispersed.

Additional variations for the coating are the covalent attachment of an antibiotic to the material of the endoprosthesis to create a permanent antibacterial surface. In a second step a compound of formula (Ia) and/or (Ib) is applied. This layer may contain at least one further antibiotic. This may be the antibiotic, which is covalently bound to the surface of the endoprosthesis or is a second antibiotic. Herein, the combinations of antibiotics or mixtures of antibiotics with other active agent(s) have to be individually adjusted and thus implemented in the interests of the patient.

A biodegradable polymer which may be comprised in a base coat, a top layer or the additional active agent layer can be selected from the group comprising or consisting of polyvalerolactones, poly-ε-decalactones, polylactonic acid, polyglycolic acid, polylactides, polyglycolides, copolymers of the polylactides and polyglycolides, poly-ε-caprolactone, polyhydroxybutyric acid, polyhydroxybutyrates, polyhydroxyvalerates, polyhydroxybutyrate-co-valerates, poly(1,4-dioxane-2,3-diones), poly(1,3-dioxane-2-ones), poly-para-dioxanones, polyanhydrides such as polymaleic anhydrides, polyhydroxymethacrylates, fibrin, polycyanoacrylates, polycaprolactone dimethylacrylates, poly-β-maleic acid, polycaprolactonebutyl-acrylates, multiblock polymers such as from oligocaprolactonedioles and oligodioxanonedioles, polyetherester multiblock polymers such as PEG and poly(butyleneterephthalate), polypivotolactones, polyglycolic acid trimethyl-carbonates, polycaprolactone-glycolides, poly(γ-ethylglutamate), poly(DTH-iminocarbonate), poly(DTE-co-DT-carbonate), poly(bisphenol-A-iminocarbonate), polyorthoesters, polyglycolic acid trimethyl-carbonates, polytrimethyl carbonates, polyiminocarbonates, poly(N-vinyl)-pyrrolidone, polyvinylalcohols, polyesteramides, glycolated polyesters, polyphosphoesters, polyphosphazenes, poly[p-carboxyphenoxy)propane], polyhydroxypentanoic acid, polyanhydrides, polyethylene oxide-propylene oxide, soft polyurethanes, polyurethanes with amino acid residues in the backbone, polyetheresters such as polyethylene oxide, polyalkeneoxalates, polyorthoesters as well as their copolymers, lipids, carrageenanes, fibrinogen, starch, collagen, protein based polymers, polyamino acids, synthetic polyamino acids, zein, modified zein, polyhydroxyalkanoates, pectic acid, actinic acid, modified and unmodified fibrin and casein, carboxymethyl sulphate, albumin, moreover hyaluronic acid, heparan sulphate, heparin, chondroitine sulphate, dextran, β-cyclodextrines, and copolymers with PEG and polypropyleneglycol, gummi arabicum, guar, gelatine, collagen, collagen-N-hydroxysuccinimide, lipids, phospholipids, modifications and copolymers and/or mixtures of the substances mentioned above.

A biodegradable polymer which may be comprised in a base coat, a top layer or the additional active agent layer can be selected from the group comprising or consisting of polyacrylic acid and polyacrylates such as polymethylmethacrylate, polybutylmethacrylate, polyacrylamide, polyacrylonitriles, polyamides, polyetheramides, polyethylene amine, polyimides, polycarbonates, polycarbourethanes, polyvinyl ketones, polyvinyl halides, poly vinylidene halides, polyvinyl ethers, polyvinylarenes, polyvinyl esters, polyvinyl pyrrollidones, polyoxymethylenes, polyethylene, polypropylene, polytetrafluoro-ethylene, polyurethanes, polyolefine elastomers, polyisobutylenes, EPDM gums, fluorosilicones, carboxymethyl chitosans, polyethylene terephthalate, polyvalerates, carboxymethylcellulose, cellulose, rayon, rayon triacetates, cellulose nitrates, cellulose acetates, hydroxyethyl cellulose, cellulose butyrates, cellulose acetate butyrates, ethyl vinyl acetate copolymers, polysulphones, epoxy resins, ABS resins, EPDM gums, silicones such as polysiloxanes, polyvinyl halogens and copolymers, cellulose ethers, cellulose triacetates, chitosan, and copolymers and/or mixtures thereof.

Endoprostheses coated according to the invention can be manufactured using a process for coating, which is based on following principle:
 a. Providing an uncoated endoprosthesis or an endoprosthesis which is furnished with a base coat and
 b. substantially complete coating of the surface with a coating solution comprising at least one antibiotic and a substance of the general formula (Ia) and/or (Ib)

After coating the endoprosthesis according to the invention with a coating solution containing at least one antibiotic and a substance of the general formula (Ia) or (IB), after evaporation or removal of the solvent an antibiotic-releasing, anti-inflammatory and germicidal formulation is obtained, which extends the use of hydrophilic active agents also to hydrophobic systems.

The surfaces of the endoprosthesis, preferably of the bone-contacting implant, to come in contact with bone or tissue are coated. Corresponding surfaces of the implant, i.e. surfaces of the implant, which come or may come into contact with other surfaces of the implant do not require a coating according to the invention. The term "corresponding surface area" is known to the skilled person. An example of corresponding surfaces is the surface of the tibial component of an artificial intervertebral implant, which can come in contact with the onlay.

Typically, the coating process will be repeated once or twice or three times, wherein this is not mandatory. Also, a single coating process may be sufficient to apply the necessary amount of the antibiotic and of the substance of the general formula (Ia) and or (Ib) onto the endoprosthesis.

The coating may also be dried by heating or actively applying a vacuum or in a gas stream. The term solution, as used herein, means also an emulsion or a dispersion and is not limited to clear, homogeneous solutions.

As the solvent for the mixture of antibiotic and substance of the general formula (Ia) and/or (Ib) and their derivatives can be used chloroform, ethanol, methanol, tetrahydrofuran, hexane, acetone, methyl acetate, ethyl acetate, methylene chloride, DMSO, or mixtures thereof with each other or water.

It is also possible to add a further non-polymeric adjuvant as a matrix into the mixture of antibiotic and substance of the general formula (Ia) and or (Ib). For example, contrast agents or contrast agents analogs, as well as biologically compatible organic compounds that improve the coating properties are suitable. However, it is preferred when the coating according to the invention of at least one antibiotic and at least one substance of the general formula (Ia) and/or (Ib) is free of polymers.

The coating is feasible as spray, dip, brush, spatter, drag, thread drag, roll and/or pipetting method and can be used universally from a procedural point of view, which means it is applicable to arbitrarily shaped surfaces.

The term "coating solution" as used herein means the mixture of the composition of at least one antibiotic agent with at least one substance of the general formula (Ia) and/or (Ib) and, and/or derivatives thereof and a solvent or solvent mixture and/or further excipient, which is a real solution, dispersion, suspension or emulsion. The term "solution" is further intended to illustrate that it is a liquid mixture, wherein the density of the liquid mixture can vary widely.

With the term "mixture" or "mix" the combination of at least two compounds is meant, which are present in the coating solution. In the mixture of two compounds, no new compound must arise. But the definition of the term "mixture" as used herein, also includes the formation of new compounds from a combination of at least two compounds. Thus chemical reactions between the at least two compounds are explicitly included. The mixture may be a batch, an alloy, a polymer, a co-polymer, a composite, a sponge, foam, a solution, a suspension, an emulsion, or dispersion. In particular, it may be homogeneous mixtures consisting of one phase and also heterogeneous mixtures with two more phases. The definition of the term "mixture" or "mix" includes explicitly also that the compounds in the mixture may no longer be separated into its starting materials and it is also possible that the compounds lose their original properties or get new ones. It is possible that the compounds in the mixture are connected via ionic, covalent, van der Waals or hydrogen bonds with each other.

In general, an amount of 1 µg to 500 µg of antibiotic per $cm^2$ surface of the endoprosthesis to be coated, preferably an amount of 10 µg to 200 µg of antibiotic per $cm^2$ surface, and more preferred an amount of 20 µg to 100 µg of antibiotic per $cm^2$ surface are applied. Per endoprosthesis preferably 0.5 to 1000 mg of antibiotic, and more preferably 3 mg to 200 mg per endoprosthesis are applied to the endoprosthesis. However, this varies greatly depending on the size of the endoprosthesis to be coated, the type of the endoprosthesis to be coated, the surface texture and the used antibiotic. The ratio of the at least one antibiotic to the at least one substance of the general formula (Ia) and/or (Ib) is preferably between 3:1 and 1:10, particularly preferably between 1:1 and 1:5.

Endoprostheses are generally implants, which remains permanently in the body and replace the damaged body part in whole or in part. The term "endoprosthesis" as used herein also includes, in addition prostheses and implants, which remain not permanently in the body but over an extended period (at least in the range of several days). One exemplary and not exhaustive list of the endoprosthesis in accordance with this invention thus includes dental implants, pacemakers, stents, vascular grafts, brain pacemakers, artificial hearts, port catheter, orthopedic implants, eye implants such as visual implants, retina, vitreous body or cornea, skull reconstructions, bone replacement, penile prostheses, sphincter prostheses, cochlear implants, catheters, urinary catheters, breathing hoses, venous catheters and cannulae. Particularly preferred are orthopedic implants used in the field of the skeleton.

As example of such orthopedic implant may be mentioned: spinal implants, hip joint implants, hip sockets, shoulder joint implants, elbow implants, finger joint implants, ankle implants, toe joint implants, knee implants, subtalar joint implants, wrist implants or general joint implants, implants for the fusion of bone, radial head implants, pedicle screws, anchoring pins of implants or for implants, implants for the skull, angle implants, bone wedges, bone screws, intervertebral implants, like cages or artificial discs or spinous process distractor, bone balloons for kyphoplastie, implants for osteotomies (high tibial osteotomy), metatarsal surgery, hindfoot surgery or general implants, which connect bones or are at least partially inserted into bone. A particularly preferred orthopedic implant is a joint implant, in particular a hip joint implant. A hip joint implant can be both a head prosthesis and a shaft prosthesis (prosthesis stem or shaft of the femur) and acetabular cup prosthesis.

The aforementioned implants usually consist completely of a hard material, especially a metal or metal alloy such as titanium, zirconium, oxidized zirconium, hafnium, platinum, rhodium, niobium, surgical stainless steel, CoCr-steel (cobalt-chromium), tantalum but can also be made of fiber reinforced plastics (glass-/carbon-fibers with a corresponding matrix), PEEK [poly(ether etherketone)], or polymer materials in general. Moreover, metals such as aluminum, medical steel, and/or gold can be added to the metal alloys.

Endoprosthesis are generally made of biocompatible materials, which can be very different depending on the area of application. The surface of the endoprostheses to be coated may be hydrophilic or hydrophobic, rough or smooth also microporous or macroporous and other textured surfaces are suitable. It is also possible that the endoprosthesis have already been coated prior to application of the coating according to the invention (with a base coating) or are pretreated in any other form.

The aforementioned implants may also have ceramic coatings for curing, whereupon the coatings of the present invention are applied.

Furthermore it has been found that a coating method of the following type solves the present problem very well.

This method for coating of an endoprosthesis comprises the following steps:
a) providing an uncoated or coated endoprosthesis,
b) providing a coating solution containing at least one antibiotic and a substance of formula (Ia) and/or (Ib) in at least one solvent,
c) applying the coating solution by spraying, dipping, brushing, painting, pipetting, vapor deposition or spattering.

It is preferred if the at least one antibiotic is present as a salt of the at least one substance of the formula (Ia) and or (Ib) in the coating or when in the coating solution the at least one antibiotic and the at least one substance of the formula (Ia) and/or (Ib) are present as anions and cations. Is especially preferred if an antibiotic pantothenate is used for the coating of the endoprosthesis.

For this purpose, a preferred, first step for coating the endoprosthesis is the preparation of a salt of the at least one antibiotic and the at least one substance of the formula (Ia) and/or (Ib), preferably by ion exchange. A solution of this salt serves then as coating solution, optionally with further adjuvants.

EXAMPLES

Figure 1:
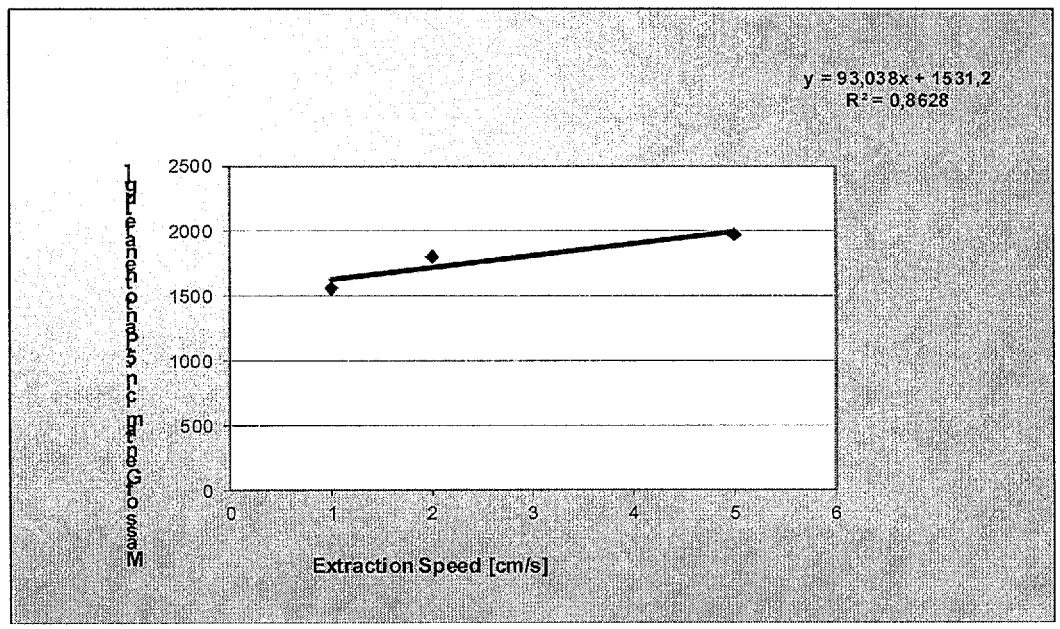
FIG. 1 shows the dependence of the surface coverage of gentamicin-penta-pantothenate on roughened titanium test specimens with increasing extraction speed.

Example 1: Preparation of Gentamicin-Penta-Dodecyl Sulfate 4.6 g sodium dodecylsulfate were solved in 37.5 mL distilled water and pooled with a second solution of 2.5 g of gentamicin sulfate in 37.5 mL distilled water. The solution is diluted with 50 mL distilled water whereby an emulsion is formed, from which then precipitations settle. The settled solid is filtered and dried.

Example 2: Preparation of Gentamicin-Penta-Pantothenate 2 g of gentamicin sulfate and 3.3 g calcium dipantothenate are dissolved in each 35 mL of deionized water and both solutions are pooled with additional 35 mL water. The solution was filtered and evaporated in a rotary evaporator at 50° C. to dryness and the precipitated solid dissolved in methanol. The methanolic suspension was subsequently centrifuged and the sediment dried overnight.

Example 3: Preparation of Tobramycin-Penta-Panthothenate 2 g of tobramycin sulfate and 3.3 g calcium dipantothenate are dissolved in each 25 mL of deionized water. Subsequently both solutions are pooled with additional 25 mL water. The resulting solution was filtered and evaporated in a rotary evaporator to dryness, and then the precipitated solid is dissolved in methanol, centrifuged and evaporated in a rotary evaporator to dryness. The resulting solid was dried overnight

Example 4: Preparation of Tobramycin-Penta-Dodecyl Sulfate 4.6 g sodium dodecylsulfate were solved in 37.5 mL distilled water and pooled with a second solution of 2.0 g of tobramycin sulfate in 37.5 mL distilled water. The solution is diluted with 50 mL distilled water whereby an emulsion is formed, from which then precipitations settle. The settled solid is filtered and dried.

Example 5: Preparation of Gentamicin as the Free Base by Ion Exchange 1 g gentamicin sulfate were dissolved in 25 mL of deionized water and 0.26 g of calcium hydroxide added. The milky suspension was filtered and the filtered solution evaporated to dryness. The residue in the flask was dissolved in methanol and then evaporated to dryness. The sulfate-free gentamicin was present in the flask as a clear, gel-like, amorphous substance.

Example 6: Preparation of Gentamicin (Free Base) by Ion Exchange Using an Anion Exchanger 5 g gentamicin sulfate were dissolved in 10 mL of deionized water and passed through a column filled with the anionic ion exchange resin "Dowex 1×2, strongly basic, Cl$^-$ form, 50-100 mesh". The eluate was collected and evaporated to dryness. The desulfated gentamicin was then dried. Previously, the resin was washed with deionized water, then basified with 4% sodium hydroxide solution and then washed to neutrality with deionized water. The resin washed to neutrality was then analyzed with silver nitrate solution to be free of chloride and again rinsed with deionized water.

Example 7: Preparation of Tobramycin Penta-Dexpanthenol 2.2 g dexpanthenol were dissolved in 75 mL methanol and then 1 g of tobramycin (see Example 5 as the free base) was added to the solution. Subsequently, the solution was evaporated to dryness.

Example 8: Preparation of Gentamicin Penta-Dexpanthenol 2 g gentamicin sulfate were in 25 mL of deionized water and 0.5 g of calcium hydroxide was added to the aqueous solution. A milky suspension results which was evaporated to dryness. The residue in the flask was dissolved in methanol, filtered and the filtrate was then evaporated to dryness. The sulfate free gentamicin was then present as a clear, gel-like, amorphous substance. 2.2 g dexpanthenol were dissolved in 75 mL methanol and then 1 g of the gentamicin being a free base was added and evaporated to dryness.

Example 9: Preparation of Chlorhexidine Dipantothenate

Calcium dipantothenate was added to 0.5 M sulfuric acid and the aqueous pantothenic acid solution evaporated to dryness. The residue in the flask was dissolved in methanol and evaporated again to dryness. Then the dried pantothenic acid was weighed, dissolved in 75 mL of methanol and treated with chlorhexidine (free base) in the relation pantothenic acid to chlorhexidine 2:1 and evaporated to dryness.

The chlorhexidine dipantothenate crystallized as a brittle white solid. The stoichiometric ratio 2:1 could be accurately detected by HPLC.

Example 10: Detection of Amino Glycosides by HPLC Analysis

Here, the detection of gentamicin sulfate and gentamicin-penta-pantothenate is described as an example. Gentamicin sulfate and Gentamicin-penta-pantothenate were stained with an ortho-phthalaldehyde containing reagent and then analyzed by HPLC.

100 µL of the amino glycoside-containing sample was placed in a HPLC vial and mixed with 240 µL methanol. Thereafter 160 µl of the derivatization reagent was added thereto. The samples were then heated for 20 min. at 60° C. in a drying oven and subsequently measured.

TABLE 1

Detection of gentamicin sulfate by HPLC

| Standard | Volume of stock solution [µL] | Volume of destilled water [µL] | Dilution factor | Concentration of Gentamicin sulfate [µg/mL] | Total Peak Area [µV*min] | Response [µV*min./µg] |
|---|---|---|---|---|---|---|
| 1 | 25 | 975 | 0.025 | 29.3375 | 79566 | 2712 |
| 2 | 50 | 950 | 0.05 | 58.675 | 163974 | 2795 |
| 3 | 100 | 900 | 0.1 | 117.35 | 321742 | 2742 |
| 4 | 200 | 800 | 0.2 | 234.7 | 629286 | 2681 |

TABLE 2

Detection of gentamicin penta-pantothenate by HPLC

| Sample Name | Total Peak Area [µV*min.] | Concentration of Gentamicin [µg/mL] | Nominal Value [µg/mL] | Recovery [%] |
|---|---|---|---|---|
| Blank Value | 0 | −1.98 | — | — |
| Gentamicin-penta-pantothenate | 2444747 | 914.82 | 918.54 | 99.6 |
| Gentamicin-penta-pantothenate | 2202916 | 824.14 | 918.54 | 89.72 |

Figure 2:
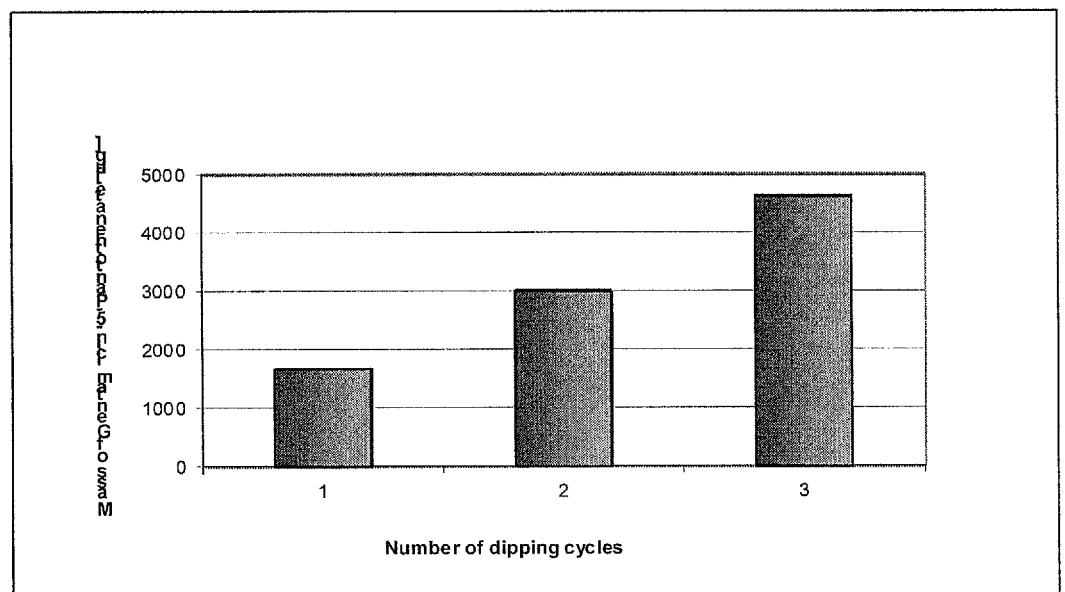
FIG. 2 shows the dependence of the surface coverage of gentamicin-penta-pantothenate on roughened titanium test specimens by repeating the dipping process.

Example 11: Dip Coating of Microporous Titanium Surfaces with Gentamicin-Penta-Pantothenate Ethanolic solutions of gentamicin-penta-pantothenate with different mass percentages (10%, 12.5%, 15%, 17.5% and 20%) were prepared. Subsequently, test specimens of titanium with a microporous surface were immersed into said coating solutions and dried after removal from the coating solution. It was shown that by increasing the extraction speed, the mass of the coating on the test specimens increases (FIG. 1). Furthermore, it was demonstrated that the mass of the coating on the test specimens increases significantly by repeating the dipping steps (FIG. 2).

Example 12: Preparation of Anhydrous Gentamicin-Penta-Pantothenate 1.65 g calcium dipantothenate were dissolved in 25 mL of DMSO at room temperature and 1 g gentamicin sulfate was added. The slightly turbid solution was filtered and then precipitated in 75 mL of acetone. The precipitated solid was dissolved in 25 mL of ethanol and then evaporated to dryness. The resulting solid was further dried overnight.

Example 13: Spray Coating with Ethanolic Gentamicin-Penta-Pantothenate Solutions Gentamicin-penta-pantothenate is spray onto roughened titanium surfaces. For this purpose, cylindrical roughened test specimens of titanium with a nominal surface area of 3.85 cm$^2$ were coated with different spray times, taking into account the following parameters.

Spray Interval: 15 s

Dry Interval: 30 s

Spray Solution: 0.6% ethanolic gentamicin-penta-pantothenate

TABLE 3

Amount of applied gentamicin-penta-pantothenate

| Serial Number: | Spray Cycles | Spray Times (in total) [s.] | Mass of Coating [µg] |
|---|---|---|---|
| 1 | 4 | 60 | 2025 |
| 2 | 6 | 90 | 3211 |
| 3 | 8 | 120 | 4904 |
| 4 | 7 | 105 | 3995 |
| 5 | 7 | 105 | 3946 |
| 6 | 7 | 105 | 4002 |

Figure 3:
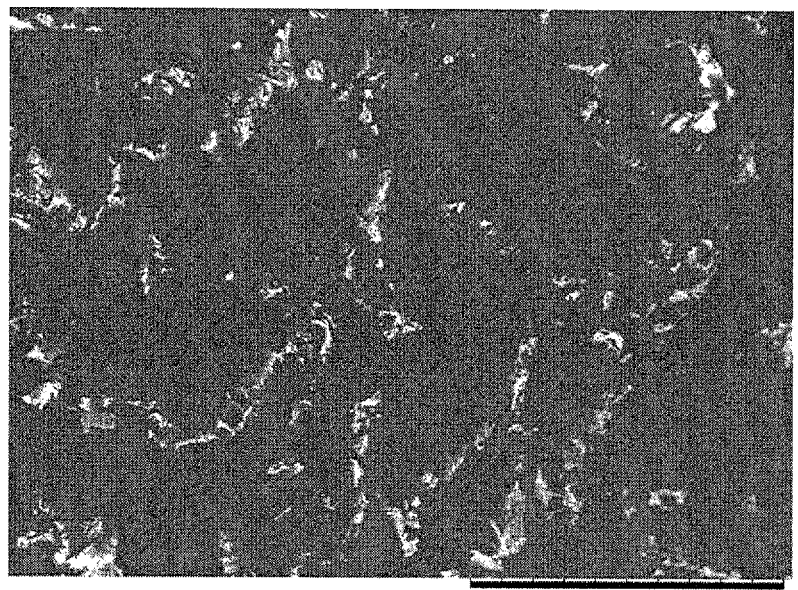
FIG. 3 shows an SEM image at 250× magnification after spray coating with ethanolic gentamicin-penta-pantothenate solution. The coating is not powdery, not brittle and fragile, but remains reliably on the surface of the endoprosthesis.
Figure 4A:
FIG. 4a Gentamicin sulfate coating (3.1 mg of gentamicin sulfate/cm$^2$) of acetone/water (v/v 1:4) applied onto preheated titanium plates with microporous titanium coating using pipetting and subsequently dried (200× magnification). The coating with the pure antibiotic is brittle, powdery and breaks off easily and is therefore unsuitable for a medical product liable to registration.
Figure 4B:
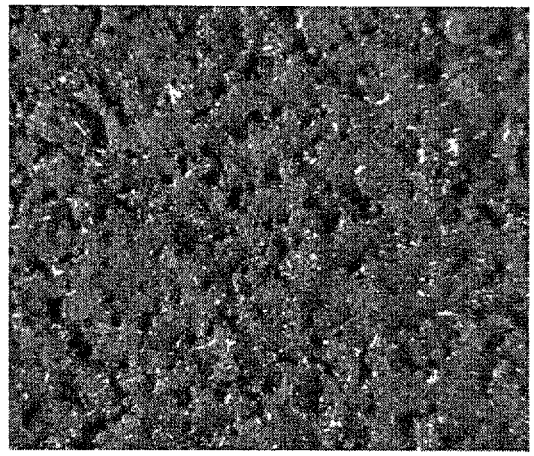
FIG. 4b Gentamicin sulfate coating (4.7 mg of gentamicin sulfate/cm$^2$) of acetone/water (v/v 1:3) applied onto preheated titanium plates with microporous titanium coating using pipetting and subsequently dried. The coating was applied in 30 single spray coating steps with intermediate drying (200 times magnification). Even with spray coating the pure antibiotic coating cannot be improved and is brittle, powdery and breaks off easily, so the actual effective dose cannot be verified and the therapeutic effect is called into question.
Figure 5:
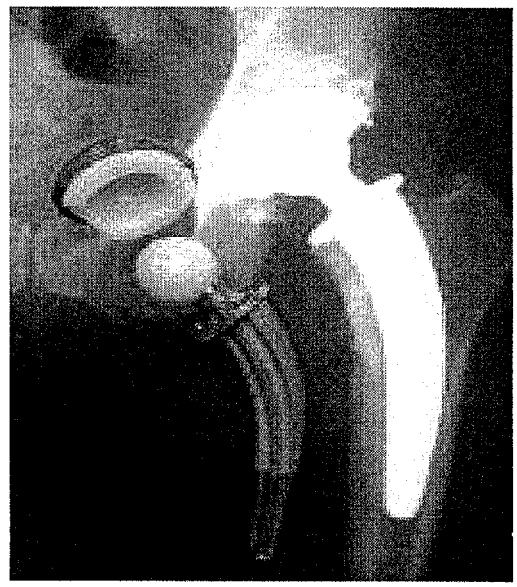
FIG. 5 Anti-infectively coated hip prosthesis and demonstration of the placement by x-ray FIG. 6 In vitro experiments show, that there is no controlled in vitro release of gentamicin palmitate (within 11 days) but rather high initial concentration without apparent release delay, wherein, compared to gentamicin pantothenate and gentamicin pantothenate/PVP with 100% release, only 58% of gentamicin are released.
Figure 6:
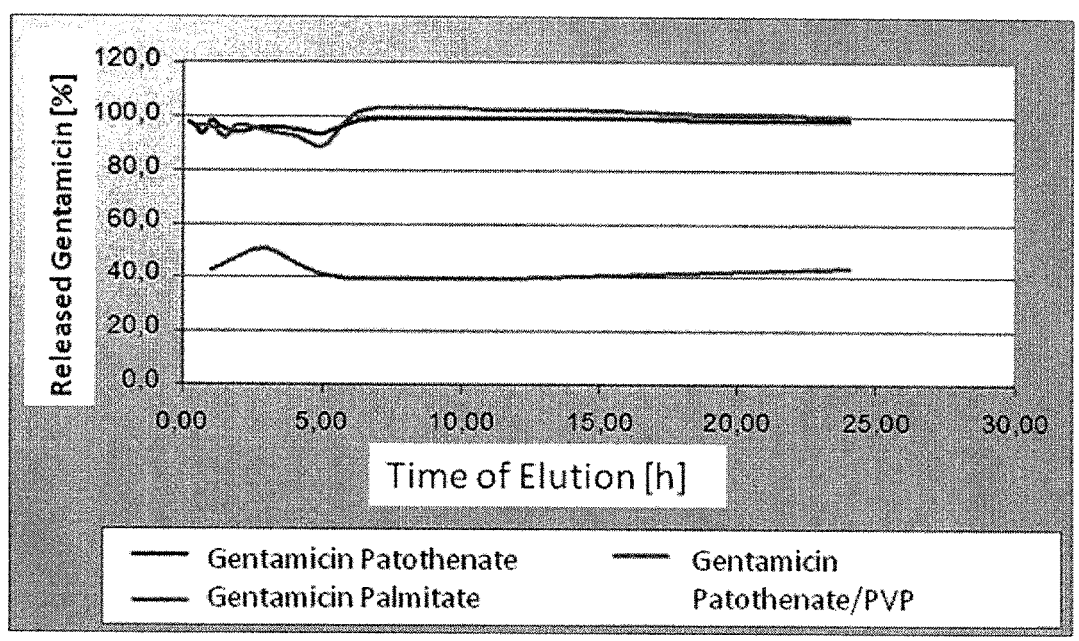

On the surface a uniform amorphous coating was formed, which is very well visible on electron micrographs (FIG. 3).

Example 14: Coating of an Endoprosthesis with Gentamicin-Penta-Pantothenate in Combination with Daptomycin or Vancomycin 0.6% ethanolic gentamicin-penta-pantothenate is mixed with a 0.5% ethanolic daptomycin (or vancomycin) solution (1:1, v/v) and sprayed evenly on a hip joint prosthesis made of medical grade stainless steel. The coating is either located directly on the surface of the prosthesis, or is applied to an exemplarily with a biodegradable or a biostable polymer or a hydroxyapatite coated surface of the prosthesis.

Example 15: Coating of Endoprostheses with Gentamicin-Penta-Pantothenate and a Porous Polysulfone Toplayer as an Example of a Coating with an Additional Active Agent Layer The gentamicin-penta-pantothenate produced according to experiment 12 is pipetted as a 20% ethanolic solution to a knee prosthesis. After evaporation of the solvent, in a further step, a polysulfone/PVP solution (for example, 0.80% PS, 0.08% PVP, or for example 0.84% PS, 0.04% PVP in chloroform) was applied by spraying. Either again gentamicin or another substance such as another antibiotic like vancomycin, fusidic acid, rifampicin, etc., or drugs such as paclitaxel, rapamycin can be added to the polysulfone spray solution.

Suitable spray solutions for such an additional active agent coating maybe:
Spray Solution: 0.58% PS, 0.22% simvastatin, 0.08% PVP in chloroform
Spray Solution: 0.58% PS, 0.08% PVP, 0.22% paclitaxel in chloroform
Spray Solution: 0.62% PS, 0.22% simvastatin, 0.04% PVP in chloroform
Spray Solution: 0.66% PS, 0.22% simvastatin in chloroform
Spray Solution: 0.66% PS, 0.22% paclitaxel in acetone
Spray Solution: 0.66% PS, 0.22% 17-β-estradiol in chloroform
Spray Solution: 0.66% PS, 0.22% trapidil in chloroform
Spray Solution: 0.62% PS, 0.22% amikacin, 0.04% PVP in chloroform
Spray Solution: 0.62% PS, 0.22% gentamicin, 0.04% PVP in ethanol

Example 16: Coating of Endoprostheses with an Amino Glycoside Pantothenate and a Biodegradable Polymeric Top Layer The amino glycoside pantothenate prepared according to prescription 8 or 12 is applied by pipetting to a stent.
Subsequently, a biodegradable polymeric layer is applied equivalent to Example 15.
In the following examples of suitable spray solutions are mentioned:
Spray solution: 19.8 mg polylactide and 6.6 mg taxol are filled with chloroform up to 3 g.
Spray solution: 145.2 mg polylactide and 48.4 mg rapamycin are filled up to 22 g with chloroform.
Spray solution: 22 mg polylactide and 22 mg hydrophilic active agent are weighed in and filled with chloroform up to 20 g. Spray solution: 176 mg polylactide glycolide are weighed in and filled with chloroform up to 20 g.
Spray solution: 22 mg polylactide glycolide and 22 mg kanamycin are weighed in and filled with chloroform up to 22 g.

Example 17: Continuous Coating of Endoprosthesis with a Polymer/Antibiotic-Pantothenate Mixture Polyurethane is dissolved in THF, so as to obtain a 14% solution and mixed with an antibiotic-pantothenate of choice, so that the solution contains an active agent content of 30% by weight. This solution is diluted with THF or chloroform to 10% and applied to the surface of the endoprosthesis by immersion, spraying or pipetting.

Example 18: Coating of a Catheter with Tobramycin Pantothenate Using Pipetting For this, the tobramycin pantothenate prepared according to experiment 7 as 10% ethanol solution is evenly distributed by pipetting on the surface of the catheter and dried.

Example 19: Coating of Titanium Cylinders by Pipetting for Cytotoxicity Tests The outer surfaces of titanium cylinders were coated by pipetting with ethanolic gentamicin-penta-pantothenate solution (w=10%).

TABLE 4

Coating of titanium cylinders by pipetting with gentamicin-penta-pantothenate for cytotoxicity test

| Sample | Weight of Sample | Final | Mass of the Coating | | |
|---|---|---|---|---|---|
| Nominal Load [µg/cm$^2$] | taken Average [g] | Weights Average [g] | Actual Value [mg] | Nominal Value [mg] | Coating [%] |
| 900 | 44.89078 | 44.91764 | 26.86 | 27.14 | 99.0 |
| 800 | 44.79786 | 44.82141 | 23.55 | 24.13 | 97.6 |
| 700 | 44.97982 | 45.00092 | 21.10 | 21.11 | 99.9 |

Example 20: Coating of Titanium Cylinders Using Pipetting for Proliferation Assays The outer surfaces of the titanium cylinder were (1% w) coated by pipetting with ethanolic gentamicin-penta-pantothenate solution.

TABLE 5

Coating of titanium cylinders with gentamicin-penta-pantothenate using pipetting for the proliferation assay

| Sample | Weight of Sample | Final | Mass of the Coating | | |
|---|---|---|---|---|---|
| Nominal Load [µg/cm$^2$] | taken Average [g] | Weights Average [g] | Actual Value [mg] | Nominal Load [mg] | Coating [%] |
| 100 | 44.76058 | 44.76332 | 2.74 | 3.02 | 90.9 |
| 50 | 44.86333 | 44.86472 | 1.39 | 1.51 | 92.0 |
| 20 | 44.87962 | 44.88018 | 0.56 | 0.60 | 92.3 |

Example 21: Dose Finding for Samples for Coating of Hip Prostheses with Gentamicin Penta-Pantothenate The experiments serve for determining the loading amount of gentamicin pantothenate/cm$^2$, which shows as lower limit sufficient antibacterial activity and the highest loading amount as upper limit which can be used without a cytotoxic effect for the cells in the vicinity of the coated implant. For this purpose, coarse-blasted titanium cylinders were coated by pipetting with different amounts of ethanolic gentamicin-5-pantothenate solution and after drying the coating mass was determined by weighing. The coated titanium tubes were then γ-sterilized.

Approximate values for the upper limit and lower limit of the amount of coating on the test specimens were derived using data already known to cytotoxicity of gentamicin as a pure substance. For this purpose a lower limit against partially resistant *Staphylococcus aureus* strains resulted in a minimum inhibitory concentration of 64 μg/mL (Alt et al., 2004). The conversion to gentamicin pantothenate cm² resulted therewith in a mathematically required minimum dose of 28 μg/cm² as the lower limit. The upper limit of the samples was determined on the basis of model calculations in combination with experimentally specifically determined data of cytotoxicity of gentamicin sulfate. Based on the determined data, a maximum dose of 873 μg/cm² classified as safe was calculated, however, assuming that in the worst case gentamicin pantothenate is released immediately and completely.

TABLE 6 coating amounts for determination of lower and upper dosage limit on identical titanium cylinders with rough surface

| Sample No (n = 3 each) | Coating Amount [mg] | Determination of the dosage |
|---|---|---|
| 1 | 26.9 | upper limit |
| 2 | 23.6 | upper limit |
| 3 | 21.1 | upper limit |
| 4 | 0.6 | lower limit |
| 5 | 1.5 | lower limit |
| 6 | 3.0 | lower limit |

Example 22: Tests for Antimicrobial Activity

The gentamicin-penta-pantothenate coating of cylindrical test specimens of titanium was removed with 6 mL of water (extraction volume was calculated according to an unfavorably high liquid column between the implant and bone of 2 mm with a sample surface area of 30 cm²) and incubated for 24 h at 30-35° C. Then, the minimum inhibitory concentration (MIC) for *Staphylococcus aureus* (ATCC 6538) is determined over a serial dilution series according to DIN 58940 (Part 7).

TABLE 7

Calculation of the required dosage of gentamicin-penta-pantothenate for effective antimicrobial activity (lower limit)

| Sample | MIC (Dilution of Test Solution) | calculated MIC |
|---|---|---|
| Ti-Cylinder, uncoated | not achieved | — |
| Ti-Cylinder, rough surface, 20 μg/cm² gentamicin-penta-pantothenate | 1:2 | 50 μg/mL |
| Ti-Cylinder, rough surface, 50 μg/cm² gentamicin-penta-pantothenate | 1:4 | 62.5 μg/mL |
| Ti-Cylinder, rough surface, 100 μg/cm² gentamicin-penta-pantothenate | 1:16 | 31.25 μg/mL |

MIC: Minimum inhibitory concentration

It has been found that even at the lowest concentration calculated from literature the minimum inhibitory concentration (MIC) is achieved.

Example 23: Determination of the Maximum Possible Dose of Gentamicin-Penta-Pantothenate to Avoid Cytotoxic Side Effects (Upper Limit)

After 24 hours of extraction of the gentamicin-penta-pantothenate coating of cylindrical test specimens made of titanium with cell culture medium and incubation of the extracts with L929 cells for 68 h at 37° C., the protein content of the samples was determined by BCA-colorimetric test according to ISO 10993-5. This allows a conclusion on the proliferation of the cells during incubation.

TABLE 8

Results for the cytotoxicity of samples with different concentrations of gentamicin-5-pantothenate

| Sample | Growth Inhibition [%] | Cytotoxic according to ISO 10993-5 |
|---|---|---|
| Ti-Cylinder, rough surface, uncoated | 15 | No |
| Ti-Cylinder, rough surface, 700 μg/cm² gentamicin-penta-pantothenate | 23 | No |
| Ti-Cylinder, rough surface, 800 μg/cm² gentamicin-penta-pantothenate | 18 | No |
| Ti-Cylinder, rough surface, 900 μg/cm² gentamicin-penta-pantothenate | 20 | No |

Example 24: Elution Experiments Using the Examples of Gentamicin Pantothenate and Gentamicin Palmitate Coated Titan Samples Therefore the samples are given in 2 mL demineralized water and maintained at 37° over a set period of time in a static aqueous system. At fixed times each 50 μL sample volume are taken. The determination of the antibiotic amount in the sample was done by means of ninhydrin color reaction. This method of determination of amount works for all antibiotics, which have amino groups, such as illustrated representatively with the example of the structure of the amino glycoside gentamicin:

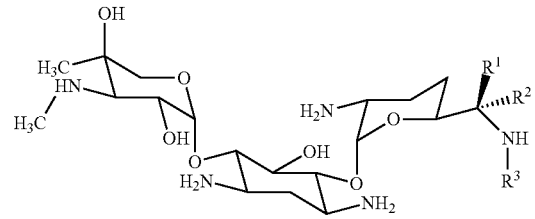

Example 25: In Vitro Cytotoxicity of Calcium Pantothenate Compared to Gentamicin Sulfate, Palmitic Acid, Salicylic Acid and Benzoic Acid The cytotoxic effect was tested on the growth inhibition of L929 cell line after incubation period of 68-72 h for 6 different concentrations according to relevant, valid DIN and ISO standards. DMEM 10% FCS was used as a negative control and the positive control was 5% DMSO in DMEM 10% FCS

TABLE 9

Comparable list of the growth inhibition of the cell line L929 in %
Samples (n = 3)

| benzoic acid | | salicylic acid | | gentamicin sulfate | | palmitic acid, | | Ca pantothenate | |
|---|---|---|---|---|---|---|---|---|---|
| c [mg/mL] | GI [%] | c [mg/mL] | GI [%] | c [mg/mL] | GI [%] | c [mg/mL] | GI [%] | c [mg/mL] | GI [%] |
| 3.0 | 77 | 1.3 | 74 | 3.0 | 29 | 0.05 | 30 | 3.0 | 2 |
| 2.1 | 64 | 1.1 | 67 | 2.4 | 22 | 0.04 | 22 | 2.4 | 1 |
| 1.5 | 50 | 0.8 | 54 | 1.8 | 12 | 0.03 | 17 | 1.8 | 7 |
| 0.9 | 35 | 0.5 | 42 | 1.2 | 12 | 0.02 | 8 | 1.2 | 4 |
| 0.6 | 20 | 0.3 | 19 | 0.6 | 8 | 0.01 | 5 | 0.6 | 0 |
| 0.3 | 10 | 0.1 | 16 | 0.3 | 4 | 0.005 | 2 | 0.3 | 0 |
| Pos. C. | 87 | | 86 | | 86 | | 88 | | 89 |
| Neg. C. | 0 | | 0 | | 0 | | 2 | | 5 |
| S.C. | 0 | | 0 | | 0 | | 0 | | 0 | a: Solvent control: 0.5% ethanol with DMEM 10% FCS, al other DMEM 10% FCS
Pos. C.: positive control
Neg. C.: negative control
S.C.: solvent control

Example 26: Preparation of Doxycycline-Di-Pantothenate 3.5 g Doxycycline hydrochloride hemiethanolate (Merck) in 50 mL 50% ethanolic solution and 3.3 g calcium pantothenate solved in 36 mL deionized water were added to each other and mixed with additional 35 mL of water. The solution was filtered and evaporated in a rotary evaporator at 50° C. to dryness and the precipitated solid was taken up in methanol. The methanolic suspension was then centrifuged and the sediment dried over night.

Example 27: Preparation of Tetracycline-Mono-Pantothenate 3.5 g tetracycline hydrochloride (Merck) in 50 mL of a 50% ethanolic solution in deionized water and 1.7 g calcium dipantothenate dissolved in 35 mL of deionized water were added to each other and combined with additional 35 mL of water. The solution was filtered and evaporated in a rotary evaporator at 50° C. to dryness and the precipitated solid was taken up in methanol. The methanolic suspension was then centrifuged and the sediment was dried overnight.

Example 28: Preparation of Minocyclin-Mono-Pantothenate 3.3 g Minocyclin hydrochloride (Sigma Aldrich) in 50 mL of a 50% ethanolic solution in deionized water and 1.7 g calcium dipantothenate dissolved in 35 mL of deionized water were added to each other and combined with additional 35 mL of water. The solution was filtered and evaporated in a rotary evaporator at 50° C. to dryness and the precipitated solid was taken up in methanol. The methanolic suspension was then centrifuged and the sediment was dried overnight.

Example 29: Preparation of Clindamycin-Mono-Pantothenate 3.3 g Clindamycinhydrochlorid (AppliChem) in 50 mL of a 50% ethanolic solution in deionized water and 1.7 g calcium dipantothenate dissolved in 35 mL of deionized water were added to each other and combined with additional 35 mL of water. The solution was filtered and evaporated in a rotary evaporator at 50° C. to dryness and the precipitated solid was taken up in methanol. The methanolic suspension was then centrifuged and the sediment was dried overnight.

Example 30: Anhydrous Preparation of Tetracycline-Mono-Pantothenate 1.65 g calcium dipantothenate is solved in 25 mL DMSO at room temperature and 3 g tetracycline hydrochloride are added. The slightly turbid solution was filtered and then precipitated in 75 mL of acetone. The precipitated solid was taken up in 25 mL of ethanol and then evaporated to dryness. The resulting solid was further dried overnight.

Example 31: Preparation of Tetracycline as Free Base by Ion Exchange 1 g of tetracycline hydrochloride was dissolved in 25 mL of deionized water and 0.26 g of calcium hydroxide added. The milky suspension was evaporated to dryness. The residue in the flask was taken up in ethanol, the resulting suspension filtered and the filtrate then concentrated to dryness. The chloride-free tetracycline was then present in the flask as a yellow amorphous solid.

Example 32: Preparation of Doxycycline as Free Base by Ion Exchange 1 g doxycycline hydrochloride hemiethanolate was dissolved in 25 mL of deionized water and 0.26 g of calcium hydroxide added. The milky suspension was evaporated to dryness. The residue in the flask was taken up in ethanol, the resulting suspension filtered and the filtrate then concentrated to dryness. The chloride-free doxycycline was then present in the flask as a yellow amorphous solid.

Example 33: Preparation Oftetracycline-Mono-Dexpanthenol 2.2 g dexpanthenol were dissolved in 75 mL methanol and subsequently 1 g tetracyclin (see example 31 as free base) was added to the solution. Then the solution was evaporated to dryness.

Example 34: Preparation of Doxycycline-Mono-Dexpanthenol 2.2 g dexpanthenol were dissolved in 75 mL methanol and subsequently 1 g doxycycline (see example 32 as free base) was added to the solution. Then the solution was evaporated to dryness.

Example 35: Preparation of Gentamicin-Penta-Pantothenic Acid Methyl Ester

Pantothenic acid methyl ester was prepared according to conventional organic esterification of pantothenic acid and methanol. 2 g gentamicin sulfate were added to 25 mL of deionized water and 0.5 g of calcium hydroxide in aqueous solution. A milky suspension resulted which was evaporated to dryness. The residue in the flask was taken up in methanol, filtered and then the filtrate was evaporated to dryness. The sulfate-free gentamicin exists thereafter as a clear, gel-like, amorphous substance. 2.2 g pantothenic acid methyl ester were dissolved in 75 mL methanol and then 1 g of this free base gentamicin was added and evaporated to dryness.

Example 36: Preparation of Gentamicin-Penta-Panthenyl Ethyl Ether 2 g gentamicin sulfate were dissolved in 25 mL of deionized water and 0.5 g of calcium hydroxide added to the aqueous solution. A milky suspension resulted which was evaporated to dryness. The residue in the flask was taken up in methanol, filtered and subsequently the filtrate was concentrated to dryness. The sulfate-free gentamycin was then present in the flask as a clear, gelly, amorphous solid. 2.2 g panthenyl ethyl ether (Sigma Aldrich, also named pantothenyl ethyl ether) were dissolved in 75 mL methanol and then 1 g of this free base gentamicin was added and evaporated to dryness.

Example 37: Preparation of Gentamicin-Penta-Panthenyl Triacetate

Panthenyl triacetate was synthesized according to U.S. Pat. No. 6,982,346B2 using dexpanthenol and acetic anhydride. Afterwards 2 g gentamicin sulfate in 25 mL of deionized water and 0.5 g of calcium hydroxide were added to the aqueous solution. A milky suspension developed which was evaporated to dryness. The residue in the flask was taken up in methanol, filtered and then the filtrate was evaporated to dryness. The sulfate-free gentamicin was then a clear, gel-like, amorphous substance. 2.8 g panthenyl triacetate were dissolved in 75 mL methanol and then 1 g of gentamicin being a free base was added and evaporated to dryness.

Example 38: Preparation of Gentamicin-Penta-Panthenyl Monoacrylate

Panthenyl monoacrylate (also named pantothenyl monoacrylate) was synthesized according to WO2008053051 from dexpanthenol and methyl acrylate. Afterwards 2 g gentamicin sulfate in 25 mL of deionized water and 0.5 g of calcium hydroxide were added to the aqueous solution. A milky suspension developed which was evaporated to dryness. The residue in the flask was taken up in methanol, filtered and then the filtrate was evaporated to dryness. The sulfate-free gentamicin was then a clear, gel-like, amorphous substance. 2.2 g panthenyl monoacrylate were dissolved in 75 mL methanol and then 1 g of this free base gentamicin was added and evaporated to dryness.

Example 39: Dip Coating of a Microporous Anchoring Pin with Tetracycline-Mono-Pantothenate Ethanolic tetracycline mono-pantothenate solutions having different amounts (10%, 12.5%, 15%, 17.5% and 20%) were prepared. It was demonstrated that the coating mass on the test specimens increases by increasing the extraction speed. Furthermore, it has been found that the coating amount on the test specimens increases significantly by repeating the dipping steps. Further it could be shown that the film thickness per dipping step increases proportionally by increasing the concentration of tetracycline mono-pantothenate solutions.

Example 40: Dip Coating of a Microporous Detal Prosthesis with Clindamycin-Mono-Pantothenate Ethanolic clindamycin mono-pantothenate having different amounts (10%, 12.5%, 15%, 17.5% and 20%) were prepared. It was demonstrated that the coating mass on the test specimens increases by increasing the extraction speed. Furthermore, it has been found that the coating amount on the test specimens increases significantly by repeating the dipping steps. Further it could be shown that the film thickness per dipping step increases proportionally by increasing the concentration of clindamycin mono-pantothenate solutions.

Example 41: Coating of a Finger Joint Implant with Doxycycline-Di-Pantothenate Using Pipetting For this, the doxycycline-di-pantothenate as 10% ethanolic solution prepared according to experiment 26 is evenly distributed on the surface of the catheter by pipetting.

Example 42: Coating of a Finger Joint Implant with Tetracycline-Mono-Pantothenate by Pipetting For this, the tetracycline mono-pantothenate as 10% ethanolic solution prepared according to experiment 27 is evenly distributed on the surface of the catheter by pipetting.

Example 43: Spray Coating with Ethanolic Tetracycline Mono-Dexpanthenol Solutions Tetracycline mono-dexpanthenol is sprayed onto a roughened titanium surface of a shoulder joint implant. For this purpose, the shoulder joint implants were coated using different spray times, taking into account the following parameters.

Spray interval: 15 s
Dry interval: 30 s
Spray solution: 0.4% ethanolic tetracycline mono-panthenol

TABLE 10

| Serial Number: | Spray Cycles | Spray Times (in total) [s.] | Mass of Coating [µg] |
| --- | --- | --- | --- |
| 1 | 4 | 60 | 1025 |
| 2 | 6 | 90 | 1644 |
| 3 | 8 | 120 | 2302 |
| 4 | 7 | 105 | 2001 |
| 5 | 7 | 105 | 1977 |
| 6 | 7 | 105 | 2012 |

Example 44: Spray Coating with Ethanolic Doxycycline-Di-Pantothenate Solutions Doxycycline-di-dexpanthenol is sprayed onto a roughened titanium surface of a shoulder joint implant. For this purpose, the shoulder joint implants were coated using different spray times, taking into account the following parameters.

Spray interval: 15 s
Dry interval: 30 s
Spray solution: 0.4% ethanolic doxycycline-mono-dexpanthenol

TABLE 11

| Serial Number: | Spray Cycles | Spray Times (in total) [s.] | Mass of Coating [µg] |
|---|---|---|---|
| 1 | 4 | 60 | 1618 |
| 2 | 6 | 90 | 2445 |
| 3 | 8 | 120 | 3255 |
| 4 | 7 | 105 | 3002 |
| 5 | 7 | 105 | 3021 |
| 6 | 7 | 105 | 3001 |

Example 45: Spray Coating with Ethanolic Minocyclin-Mono-Pantothenate Solutions Minocyclin-mono-pantothenate is sprayed onto a roughened titanium surface of a shoulder joint implant. For this purpose, the shoulder joint implants were coated using different spray times, taking into account the following parameters.
Spray interval: 15 s
Dry interval: 30 s
Spray solution: 0.4% ethanolic minocyclin-mono-pantothenate

TABLE 12

| Serial Number: | Spray Cycles | Spray Times (in total) [s.] | Mass of Coating [µg] |
|---|---|---|---|
| 1 | 4 | 60 | 1467 |
| 2 | 6 | 90 | 2036 |
| 3 | 8 | 120 | 2949 |
| 4 | 7 | 105 | 2455 |
| 5 | 7 | 105 | 2611 |
| 6 | 7 | 105 | 2487 |

Example 46: Coating of a an Intervertebral Implant with Gentamicin-Penta-Pantothenic Acid Methylester Gentamicin-penta-pantothenic acid methylester is first dissolved in ethanol, so that a 15% solution is formed. This coating solution is then sprayed onto an intervertebral implant made of titanium, which was previously provided with a hydroxylapatite layer. This intervertebral implant is then dried with slow rotation around the longitudinal axis of at least four hours at room temperature. Then there was a second spraying step, followed by a drying step overnight.

Example 47: Coating of a Dental Implant with Gentamycin-Penta-Panthenyl Ethyl Ether Gentamicin-penta-panthenyl ethyl ether was dissolved in ethanol to obtain a 4% solution. A screw implant made of zirconium oxide ceramic for implant into the jaw was coated by spraying with this solution. The screw portion which later comes to lie in the jaw was provided with a second layer of gentamicin penta panthenyl ethyl ether in a second coating step, so that here the coating is thicker, Therefore the upper part was covered during the second spraying step. The implant was dried for 4 hours at 37° C. in a drying oven with rotation.

Example 48: Coating of a Acetabular Prosthesis with Gentamicin-Penta-Panthenyl Triacetate Gentamicin-penta-panthenyl triacetate has been solved in methanol, so that a 7% solution was obtained. A acetabular prosthesis which is strongly roughened on its convex outer side and is provided with a tricalciumphosphate coating was selectively coated by pipetting on its concave inner side with the coating solution. Acetabular prosthesis was then dried for 6 hours at room temperature.

Measurements showed that 49 g/cm$^2$ gentamicin-penta-panthenyl triacetate were applied to the coated surface of the acetabular prosthesis.

Example 49: Coating of an Implant for Osteotomies (High Tibial Osteotomy) with Gentamicin-Penta-Panthenyl Monoacrylate Panthenyl monoacrylate has been solved in methanol, so that a 10% coating solutions results A clamp for tibial osteotomy of medical stainless steel was coated with this coating solution by pipetting and dried at 37° C. for 2 hours.

The invention claimed is:
1. Orthopedic implant characterized by an active agent coating consisting of at least one antibiotic and at least one substance of the general formula (1a) and/or (1b):

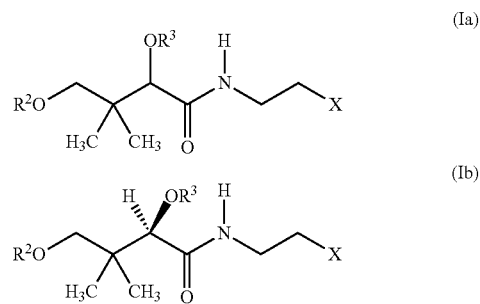

wherein
X represents —COOH, —COOR$^1$, —CH$_2$OH, or —CH$_2$OR$^1$,
R$^2$ and R$^3$ represent independently of each other —COOR$^4$, —COOR$^5$, —COR$^4$, —COR$^5$, —R$^4$, —R$^5$, or —H;
R$^1$, R$^4$ and R$^5$ represent independently of each other —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_3$H$_5$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —CH(CH$_3$)—C(CH$_3$)$_3$, —C$_7$H$_{15}$, —C$_3$H$_6$—C(CH$_3$)$_3$, —C$_4$H$_8$—CH(CH$_3$)$_2$, —C$_8$H$_{17}$, —C$_4$H$_6$—C(CH$_3$)$_3$, —C$_5$H$_{10}$—CH(CH$_3$)$_2$, —C$_9$H$_{19}$, —C$_5$H$_{10}$—C(CH$_3$)$_3$, —C$_6$H$_{12}$—CH(CH$_3$)$_2$, —C$_{10}$H$_{21}$, —C$_6$H$_{12}$—C(CH$_3$)$_3$, and —C$_7$H$_{14}$—CH(CH$_3$)$_2$, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH$_2$, —C$_3$H$_5$—CH=CH$_2$, —C$_2$H$_4$—CH=CH—CH$_3$, —CH$_2$—CH=CH—C$_2$H$_5$, —CH=CH—C$_3$H$_7$, —CH$_2$—CH=CH—CH=CH$_2$, —CH=CH—

—CH═CH—CH₃, —CH═CH—CH₂—CH═CH₂, —C(CH₃)═CH—CH═CH₂, —CH═C(CH₃)—CH═CH₂, —CH═CH—C(CH₃)═CH₂, —C₂H₄—CH═CH—CH(CH₃)═CH₂, —CH(CH₃)═CH₂—CH═CH₂, —CH₂—CH═C(CH₃)₂, —CH₂—C(CH₃)═CH—CH₃, —CH(CH₃)—CH═CH—CH₃, —CH═CH—CH(CH₃)₂, —CH═C(CH₃)—C₂H₅, —C(CH₃)═CH—C₂H₅, —C(CH₃)═C(CH₃)₂, —C(CH₃)₂—CH═CH₂, —CH(CH₃)—C(CH₃)═CH₂, —C(CH₃)═CH—CH₂, —CH═C(CH₃)—CH═CH₂, —C₄H₈—CH═CH₂, —C₃H₆—CH═CH—CH₃, —C₂H₄—CH═CH—C₂H₅, —CH₂—CH═CH—C₃H₇, —CH═CH—C₄H₉, —C₃H₆—(CH₃)═CH₂, —C₂H₄—CH(C₃)═CH—CH₂, —CH₂—CH(CH₃)—CH₂—CH═CH₂, —CH(CH₃)—C₂H₄—CH═CH₂, —C₂H₄—CH═C(CH₃)₂, —C₂H₄—C(CH₃)═CH—CH₃, —CH₂—CH(CH₃)—CH═CH—CH₃, —CH(CH₃)—CH₂—CH═CH—CH₃, —CH₂—CH═CH—CH(CH₃)₂, —CH₂—CH═C(CH₃)—C₂H₅, —CH₂—C(CH₃)═CH—C₂H₅, —CH(CH₃)—CH═CH—C₂H₅, —CH═CH—CH₂—CH(CH₃)₂, —CH═CH—CH(CH₃)—C₂H₅, —CH═C(CH₃)—C₃H₇, —C(CH₃)═CH—C₃H₇, —CH₂—CH(CH₃)—(CH₃)—CH₂, —CH(CH₃)—CH(CH₃)—CH═CH₂, —CH₂—C(CH₃)₂—CH═CH₂, —C(CH₃)₂—CH₂—CH═CH₂, —CH₂—C(CH₃)═C(CH₃)₂, —CH(CH₃)—CH═C(CH₃)₂, —C(CH₃)₂—CH═CH—CH₃, —CH(CH₃)—C(CH₃)═CH—CH₃, —CH═C(CH₃)—CH(CH₃)₂, —C(CH₃)═CH—CH(CH₃)₂, —C(CH₃)═C(CH₃)—C₂H₅, —CH═CH—C(CH₃)₃, —C(CH₃)₂—C(CH₃)═CH₂, —CH(C₂H₅)—C(CH₃)═CH₂, —C(CH₃)(C₂H₅)—CH═CH₂, —CH(CH₃)—C(C₂H₅)═CH₂, —CH₂—C(C₃H₇)═CH₂, —CH₂—C(C₂H₅)═CH—CH₃, —CH(C₂H₅)—CH═CH—CH₃, —C(C₄H₈)═CH₂, —C(C₃H₇)═CH—CH₃, —C(C₂H₅)═CH—C₂H₅, —C(C₂H₅)═C(CH₃)₂, —C[C(CH₃)₃]═CH₂, —C[CH(CH₃)(C₂H₅)]═CH₂, —C[CH₂—CH(CH₃)₂]═CH₂, —C₂H₄—CH═CH—CH═CH₂—CH₂—CH═CH—CH₂—CH═CH₂, —CH═CH—C₂H₄—CH═CH₂, —CH₂—CH═CH—CH═CH—CH₃, —CH₂—CH═CH—CH═CH—CH₃, —CH═CH—CH═CH—C₂H₅, —CH₂—CH═CH—C(CH₃)═CH₂, —CH₂—CH═C(CH₃)—CH═CH₂, —CH₂—C(CH₃)═CH—CH═CH₂, —CH(CH₃)—CH═CH—CH═CH₂, —CH═CH—CH₂—C(CH₃)═CH₂, —CH═CH—CH(CH₃)—CH═CH₂, —CH═C(H₃)—CH₂—CH═CH₂, —C(CH₃)═CH—CH₂—CH═CH₂, —CH═CH—CH═C(CH₃)₂, —CH═CH—C(CH₃)═CH—CH₃, —CH═C(CH₃)—CH═CH—CH₃, —C(CH₃)═CH—CH═CH—CH₃, —CH═C(CH₃)—C(CH₃)═CH₂, —C(CH₃)═CH—C(CH₃)═CH₂, —C(CH₃)═C(CH₃)—CH═CH₂, —CH═CH—CH═CH—CH═CH₂, —C₅H₁₀—CH═CH₂, —C₄H₈—CH═CH—CH₃, —C₃H₆—CH═(CH₃)₂, —C₆H₁₂—CH═CH₂, —C₅H₁₀—CH═CH—CH₃, —C₄H₈—CH═C(CH₃)₂, —C₇H₁₂—CH═CH₂, —C₆H₁₂—CH═CH—CH₃, —C₅H₁₀—CH═C(CH₃)₂, —C₈H₁₄—CH═CH₂, —C₇H₁₄—CH═CH—CH₃, —C₆H₁₂—CH═C(CH₃)₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —CH₂—CH(CH₃)—C≡CH, —CH(CH₃)— —CH₂—C≡CH, —CH(CH₃)—C≡C—CH₃, —C₄H₈—C≡CH, —C₃H₆—C≡C—CH₃, —C₂H₄—C≡C—C₂H₅, —CH₂—C≡C—C₃H₇, —C₄H₈—C≡C—CH, (CH₃)—C≡CH, —CH₂—CH(CH₃)—C≡CH, —CH(CH₃)—C₂H₄—C≡CH, —CH₂—CH(CH₃)—C≡C—CH₃, —CH(CH₃)—CH₂—C≡C—CH₃, —CH(CH₃)—CH(CH₃)—C≡CH, —CH(C₃H₇)—C≡CH, —C(CH₃)(C₂H₅)—C≡CH, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —CH₂—C≡C—C≡C—CH₃, —C≡C—CH₂—C≡C—CH₃, —C≡C—C≡C—C₂H₅, —C≡C—CH(CH₃)—C≡CH, —CH(CH₃)—C≡C—C≡CH, —CH(C≡CH)—CH₂—C≡CH, —C(C≡CH)₂—CH₃, —CH₂—CH(C≡CH)₂, —CH(C≡CH)—C≡C—CH₃, —C≡C—C₅H₁₁, —C₄H₈—C≡C—CH₃, —C₅H₁₀—C≡CH, —C≡C—C₆H₁₃, —C₅H₁₀—C≡C—CH₃, —C₆H₁₂—C≡CH, —C≡C—C₇H₁₅, —C₆H₁₂—C≡C—CH₃, —C₇H₁₄—C≡CH, —C≡C—C₈H₁₇, —C₇H₁₄—C≡C—CH₃, —C₈H₁₆—C≡CH,

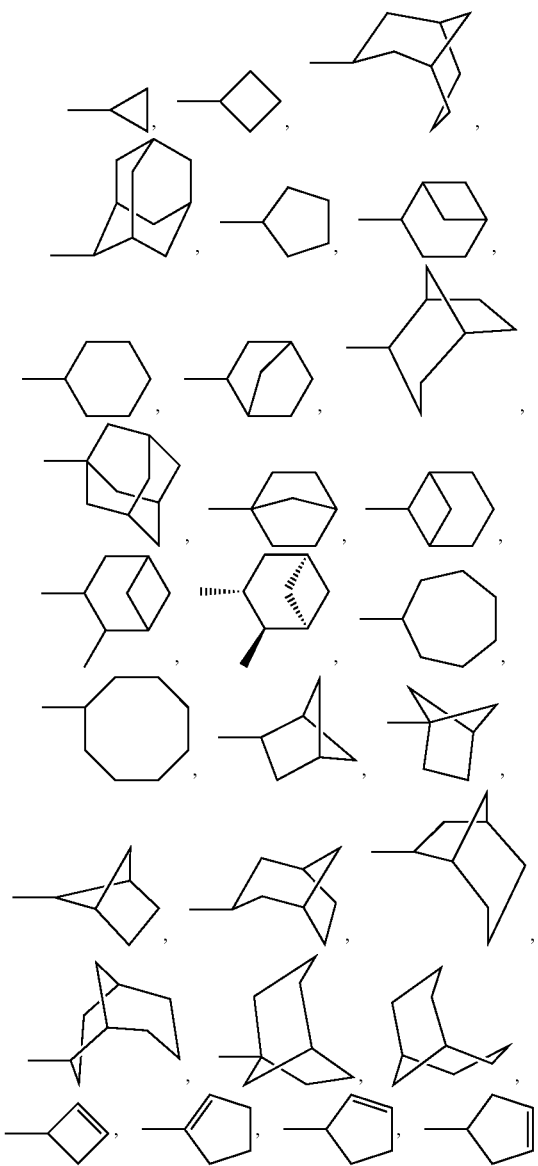

-continued

or salts, hydrates, enantiomers, diastereomers, racemates, mixtures of enantiomers, and mixtures of diastereomers of the above mentioned compounds of general formula (1a) and/or (1b); and wherein the antibiotic is selected from the group consisting of framycetin, paromomycin, ribostamycin, kanamycin, amikacin, arbekacin, bekanamycin, dibekacin, tobramycin, spectinomycin, hygromycin B, paromomycin sulfate, gentamicin, netilmicin, sisomicin, isepamicin, verdamicin, astromicin, apramycin, ansamycin, rifampicin and geneticin.

2. Orthopedic implant according to claim 1 characterized in that the at least one substance of the general formula (Ia) and/or (Ib) falls under one of the following general formulas,

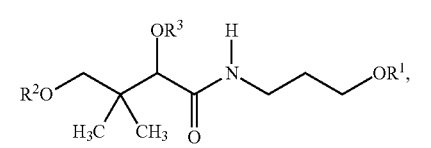 (IIa)

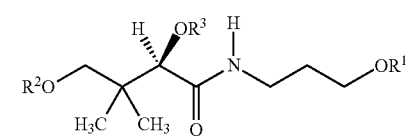 (IIb)

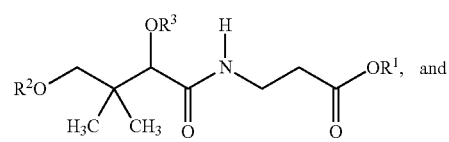 (IIIa)

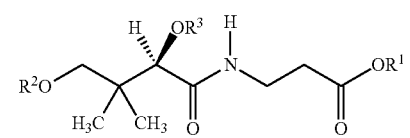 (IIIb)

wherein $R^1$, $R^2$ and $R^3$ have the meaning as defined in claim 1.

3. Orthopedic implant according to claim 1 characterized in that the at least one substance of the general formula (Ia) and/or (Ib) falls under one of the following general formulas,

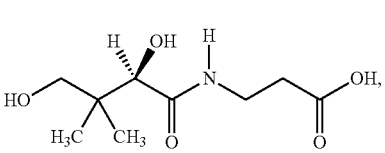 (IVa)

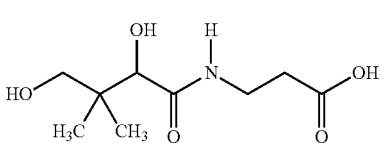 (IVb)

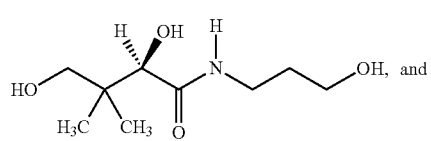 (Va)

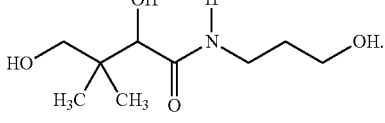 (Vb)

4. Orthopedic implant according to claim 1, wherein the orthopedic implant is selected from the group consisting of spinal implants, hip joint implants, pedicle screw, wedge of bone, bone screw, shoulder joint implants, elbow implants, intervertebral implants, finger joint implants, ankle implants, toe joints implants, knee implants, subtalar joint implants, wrist implants, implants for fusion of bone, radial head implants, anchoring pins of implants or for implants, implants for the skull, correction wedges, angle implants, implants for osteotomies (high tibial osteotomy), metatarsal surgery, and hindfoot surgery.

5. Method for coating of an orthopedic implant to provide an orthopedic implant of claim 1 comprising the following steps:
  a) providing an uncoated orthopedic implant,
  b) providing a coating solution containing at least one antibiotic and a substance of formula (1a) and/or (1b) in at least one solvent,
  c) applying the coating solution by spraying, dipping, brushing, painting, pipetting, vapor deposition or spattering.

6. Orthopedic implant according to claim 1, wherein the endoprosthesis comprises further a base coat and/or a toplayer made of polymers.

7. Orthopedic implant according to claim 6, wherein the base coat and/or the toplayer consists/consist of biodegradable polymers.

* * * * *